(12) United States Patent
Schulz et al.

(10) Patent No.: US 7,341,559 B2
(45) Date of Patent: Mar. 11, 2008

(54) PULSE OXIMETRY EAR SENSOR

(75) Inventors: Christian Schulz, Rancho Santa Margarita, CA (US); Massi E. Kiani, Laguna Niguel, CA (US); Eugene Mason, La Mirada, CA (US)

(73) Assignee: Masimo Corporation, Irvine, CA (US)

( * ) Notice: Subject to any disclaimer, the term of this patent is extended or adjusted under 35 U.S.C. 154(b) by 534 days.

(21) Appl. No.: 10/631,882

(22) Filed: Jul. 31, 2003

(65) Prior Publication Data

US 2004/0054291 A1  Mar. 18, 2004

Related U.S. Application Data

(60) Provisional application No. 60/412,281, filed on Sep. 21, 2002, provisional application No. 60/410,499, filed on Sep. 14, 2002.

(51) Int. Cl.
*A61B 5/00* (2006.01)

(52) U.S. Cl. ............ 600/309; 600/344; 600/485; 600/500

(58) Field of Classification Search ........ 600/300–301, 600/309–312, 322–326, 340, 386–394; 381/FOR. 134
See application file for complete search history.

(56) References Cited

U.S. PATENT DOCUMENTS

| | | | | |
|---|---|---|---|---|
| 4,685,464 A | * | 8/1987 | Goldberger et al. | ........ 600/344 |
| 5,413,099 A | * | 5/1995 | Schmidt et al. | ............. 600/310 |
| 5,551,423 A | * | 9/1996 | Sugiura | ...................... 600/323 |
| 5,676,139 A | * | 10/1997 | Goldberger et al. | ........ 600/310 |
| 5,792,052 A | * | 8/1998 | Isaacson et al. | ............ 600/323 |
| 5,810,724 A | * | 9/1998 | Gronvall | ..................... 600/323 |
| 5,817,008 A | | 10/1998 | Rafert et al. | |
| 6,011,986 A | | 1/2000 | Diab et al. | |
| 6,041,247 A | * | 3/2000 | Weckstrom et al. | ........ 600/323 |
| 6,152,754 A | | 11/2000 | Gerhardt et al. | |
| 6,654,621 B2 | * | 11/2003 | Palatnik et al. | ............. 600/322 |
| 2004/0115607 A1 | * | 6/2004 | Pastrick et al. | ............. 434/262 |
| 2005/0057925 A1 | * | 3/2005 | Mehler et al. | .............. 362/190 |

OTHER PUBLICATIONS

MSP Industry Alert™, vol. 3, No. 3, Fall 2001.

* cited by examiner

*Primary Examiner*—Robert L. Nasser
(74) *Attorney, Agent, or Firm*—Knobbe, Martens, Olson & Bear LLP

(57) ABSTRACT

An embodiment of an ear sensor assembly comprises an emitter pad and a detector pad. A clip is configured to removably retain each of the pads. The clip has an open position for placement on an ear tissue site and a closed position for securing the pads to opposite sides of the site. The assembly includes a sensor connector adapted to electrically communicate with a host instrument. A sensor cable has a first end terminating at the pads and a second end terminating at the sensor connector and provides electrical communications between the pads and the connector. In one embodiment, one or more silicone lenses or removable adhesive tabs aid in relieving patient discomfort and pressure necrosis.

17 Claims, 23 Drawing Sheets

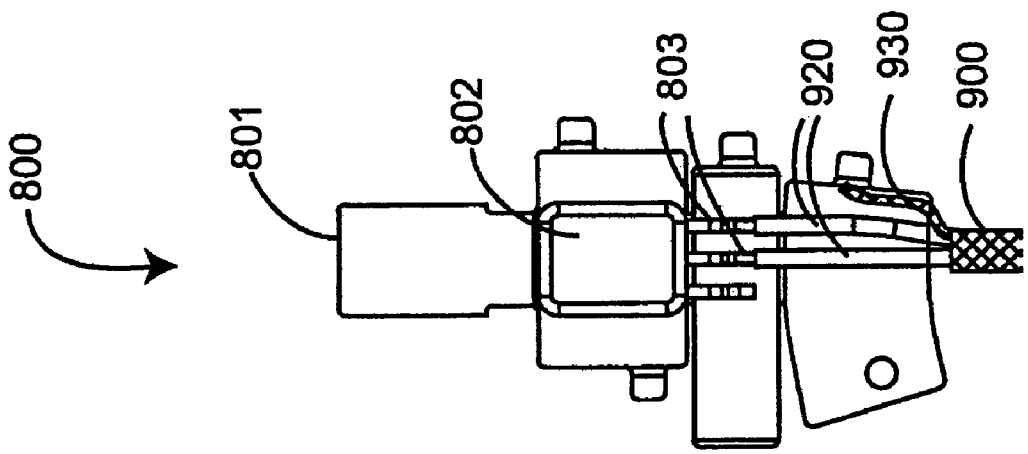
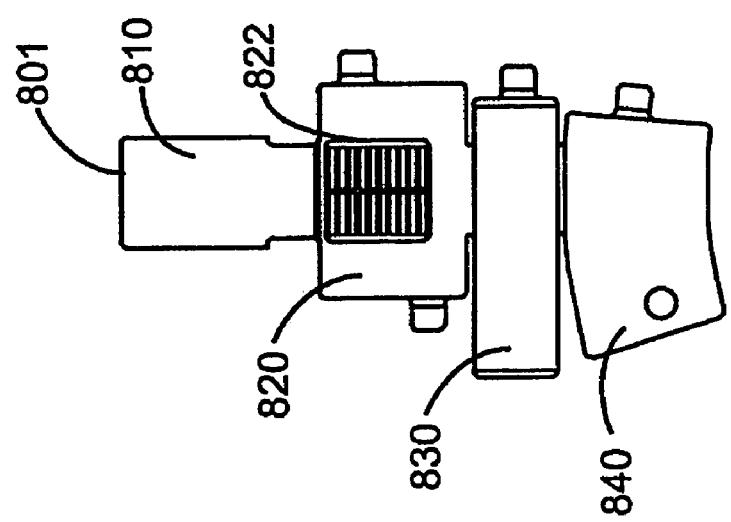
FIG. 8B
FIG. 8A

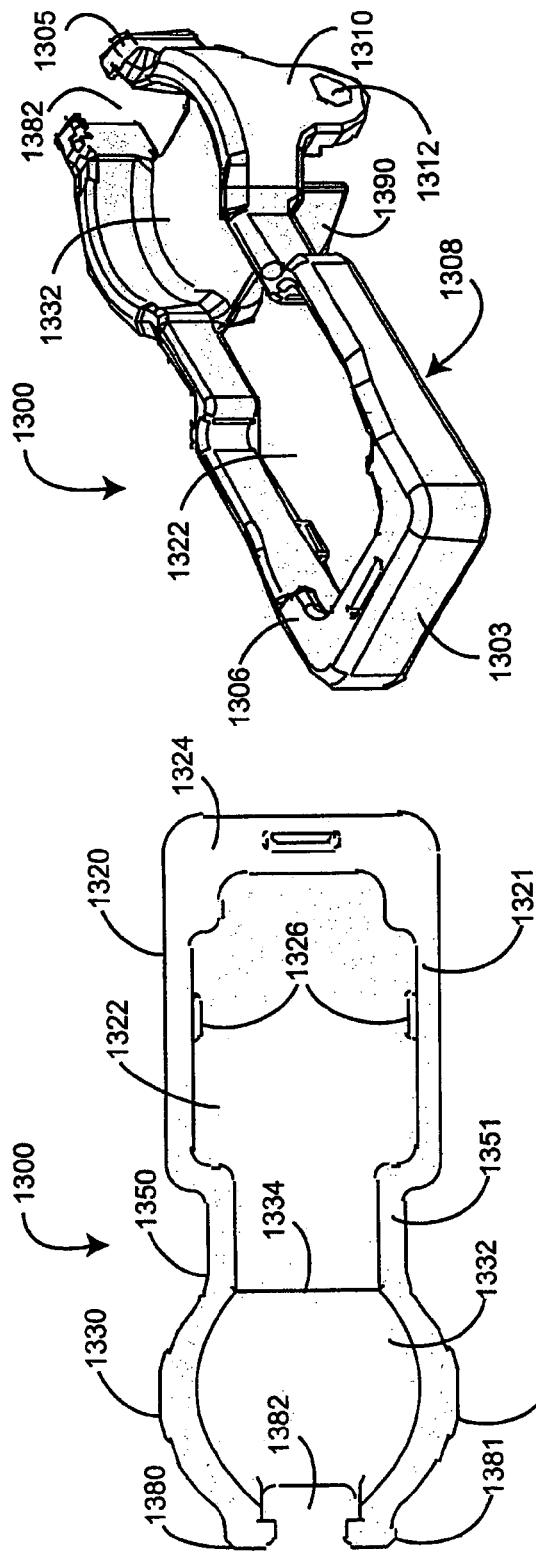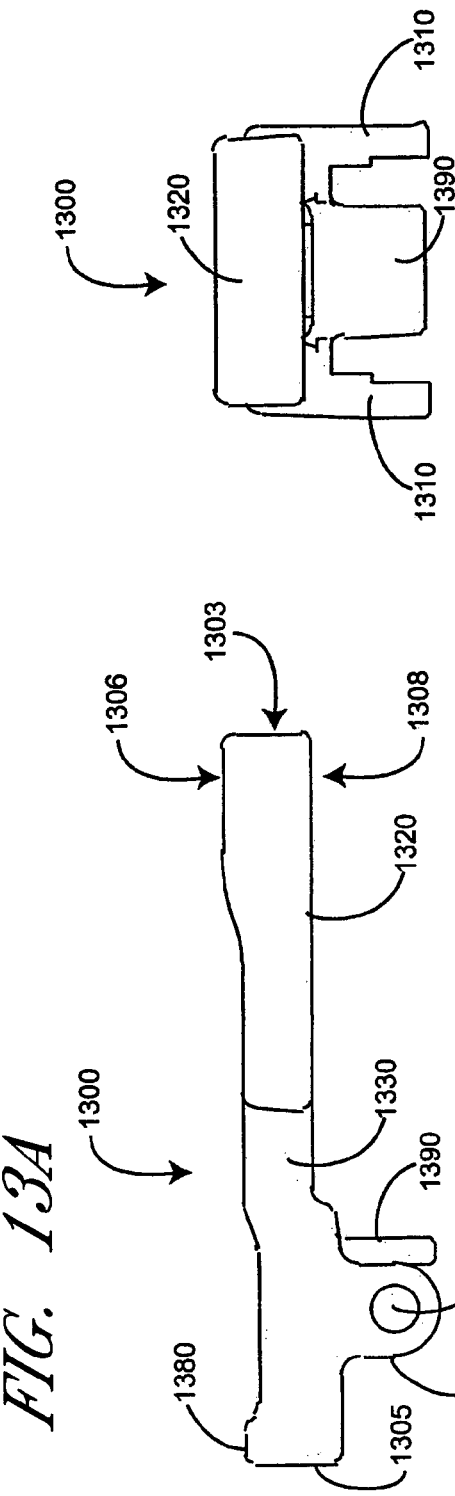

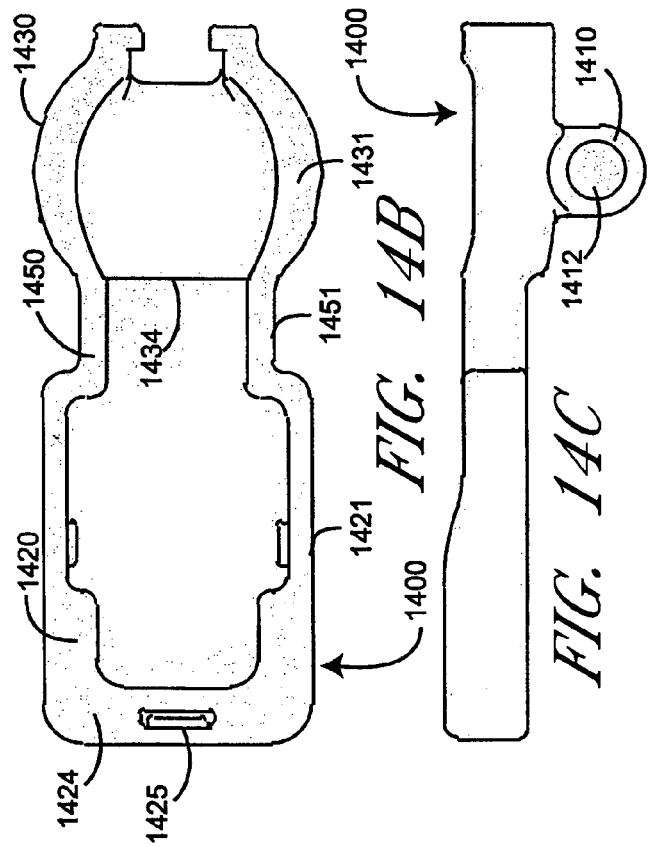
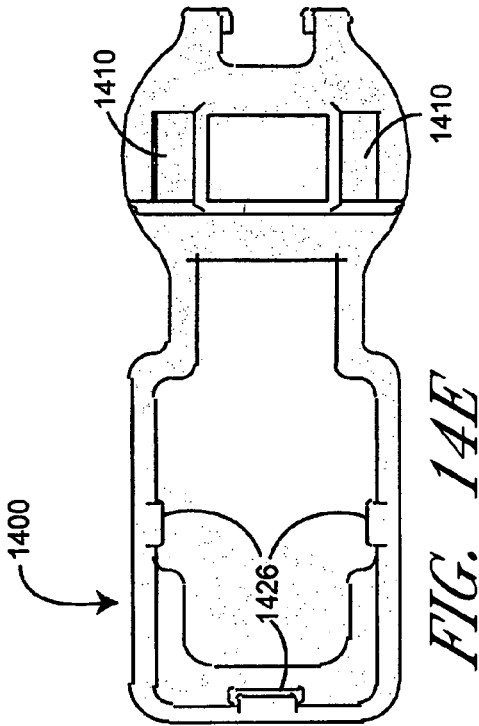
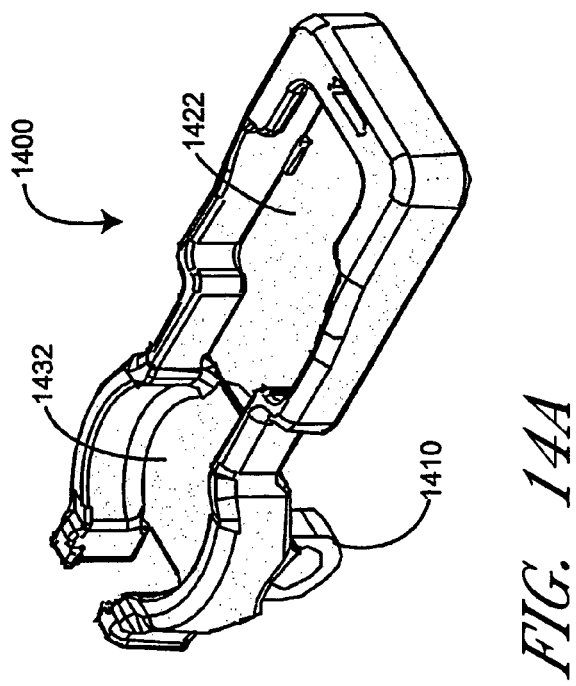
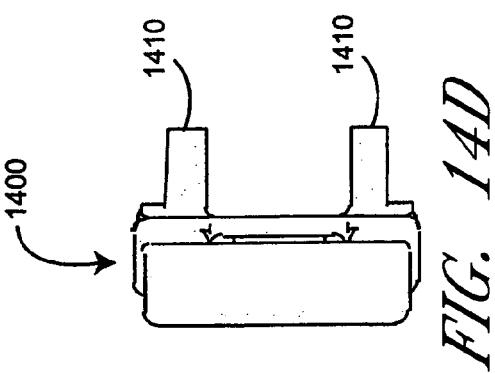
FIG. 14B
FIG. 14C
FIG. 14E
FIG. 14A
FIG. 14D

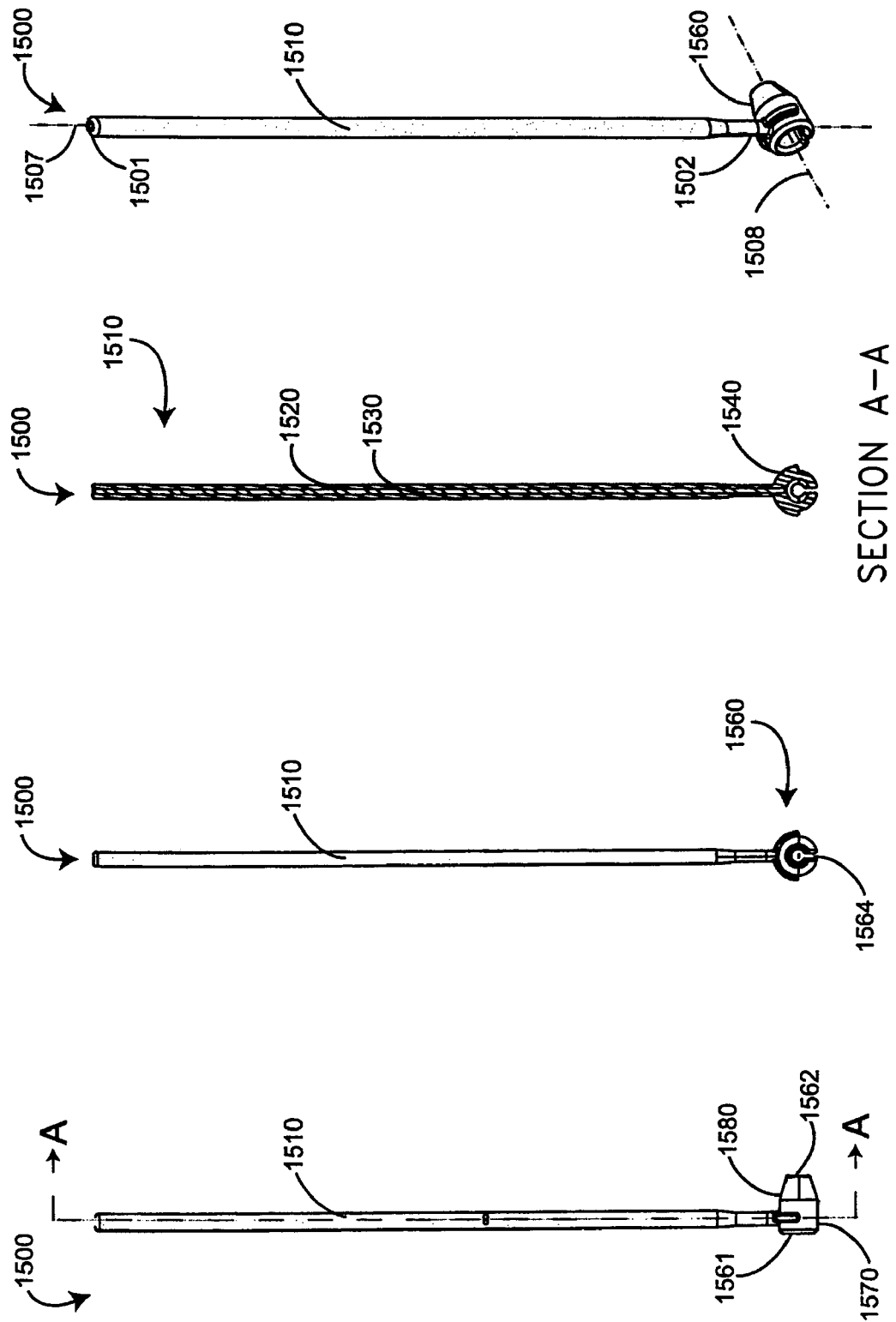

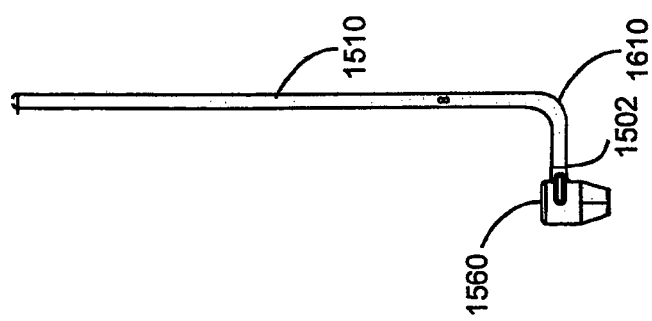
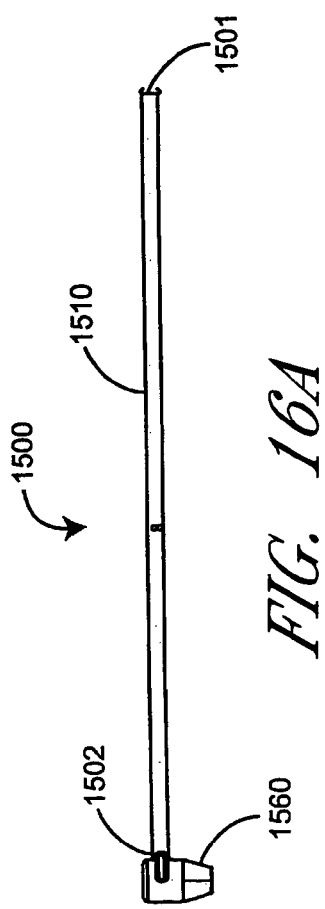
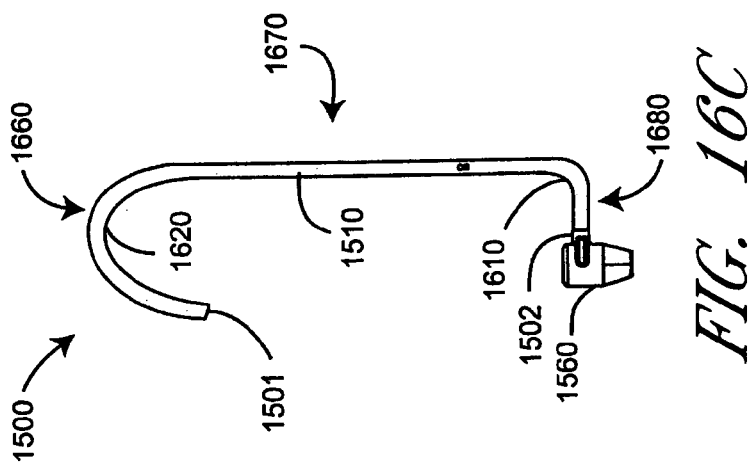

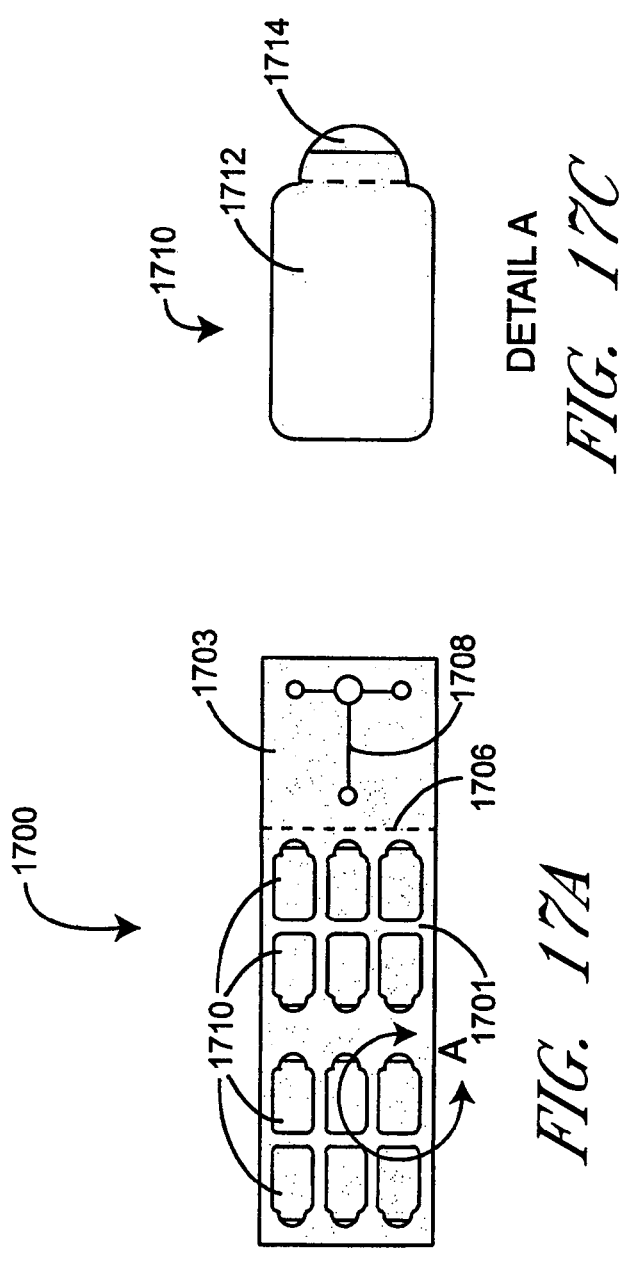
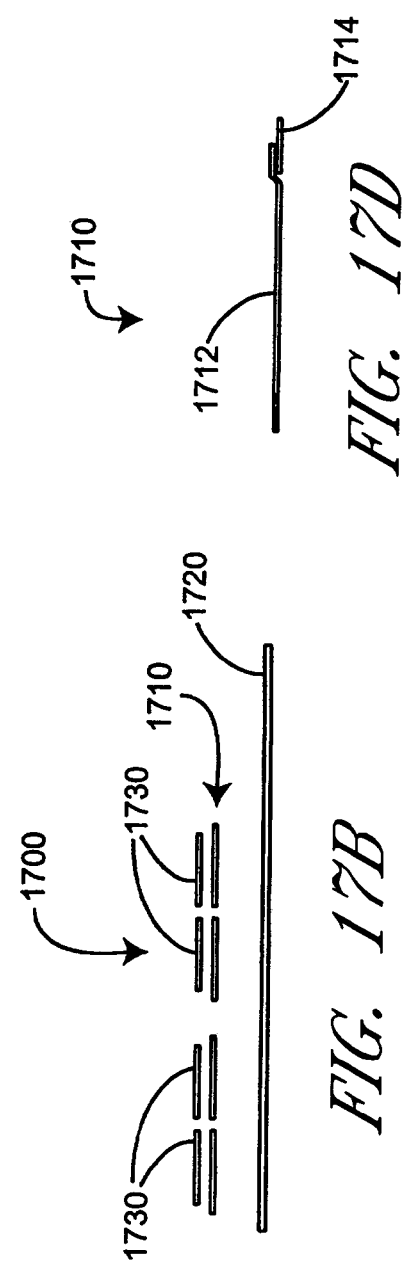

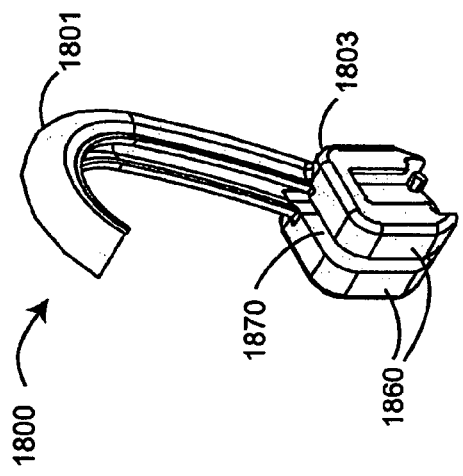
*FIG. 18B*
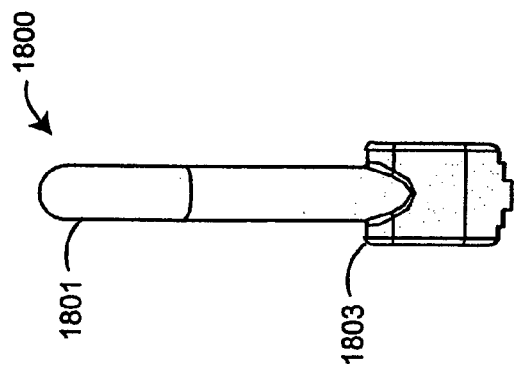
*FIG. 18D*
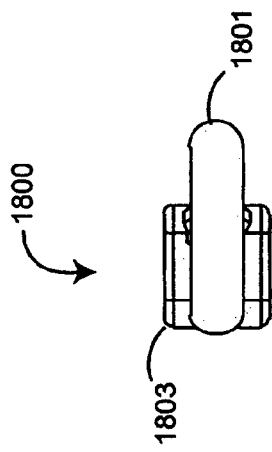
*FIG. 18A*
*FIG. 18C*

PULSE OXIMETRY EAR SENSOR

REFERENCE TO RELATED APPLICATIONS

The present application claims the benefit of U.S. Provisional Application Nos. 60/412,281, filed Sep. 21, 2002, entitled, "Pulse Oximetry Ear Sensor" and 60/410,499, filed Sep. 14, 2002, entitled, "Pulse Oximetry Ear Sensor," the disclosures of which are incorporated by reference herein.

FIELD OF THE INVENTION

The present invention relates to the field of medical devices. More specifically, the invention relates to pulse oximetry sensors.

BACKGROUND OF THE INVENTION

Pulse oximetry is a noninvasive procedure for measuring the oxygen saturation level of arterial blood, an important parameter in critical patient care applications. Pulse oximeters generally perform a spectral analysis of the pulsatile component of arterial blood in order to determine the relative concentration of oxygenated hemoglobin, the major oxygen carrying constituent of blood, to depleted hemoglobin. A pulse oximetry system includes of a sensor and a monitor. The sensor includes emitters generally having at least one red light emitting diode (LED) and at least one infrared LED that project light through blood vessels and capillaries underneath a tissue site, such as a fingernail bed. The sensor also has a detector typically consisting of a photodiode positioned opposite the LEDs so as to detect the emitted light as it emerges from the tissue site. Pulse oximeters have gained rapid acceptance in a wide variety of medical applications, including surgical wards, intensive care units, general wards and home care by providing early detection of decreases in the arterial oxygen supply and thereby, reducing the risk of accidental death and injury.

SUMMARY OF THE INVENTION

A pulse oximetry sensor may be attached to a variety of tissue sites including a finger, a foot, an ear, a forehead, and the like. An ear site has the advantage of providing a fast response to central changes in oxygenation or lack thereof. Conventional ear sensors, however, have the disadvantage of constricting the ear site because such designs use the monitoring site to secure sensor attachment.

One aspect of a pulse oximetry ear sensor is an assembly configured to relieve patient discomfort and pressure necrosis. The assembly comprises an emitter pad and a detector pad, along with a clip configured to removably retain each of the pads. The clip has an open position for placement on an ear tissue site and a closed position for securing the pads to opposite sides of the site. The assembly includes a sensor connector adapted to electrically communicate with a host instrument. A sensor cable has a first end terminating at the pads and a second end terminating at the sensor connector and provides electrical communications between the pads and the connector. In one embodiment, the assembly includes an attachment supplement configured to assist the clip in securing the pads to the ear tissue site.

Another aspect of a pulse oximetry ear sensor are the steps of assembling a sensor with an attachment, positioning the sensor against an ear tissue site with the attachment and supplementing the attachment so as to reduce pressure on said site. A further aspect of a pulse oximetry ear sensor is a sensing means for transmitting and receiving an optical signal to and from a tissue site, an attachment means for securing the sensing means to the site and a supplemental means for assisting the attachment means in securing the sensing means to the site.

Yet another aspect of a pulse oximetry ear sensor is one or more silicone lenses that can be incorporated into a clip type oximetry sensor and can aid in relieving patient discomfort and pressure necrosis. In one embodiment, the lenses can provide grippy surfaces in contact with the patient's skin, which helps to keep the sensor from slipping off the patient's earlobe or other suitable tissue site. The silicone lenses can also provide pliable contact surfaces that accommodate the patient's skin shape and help to relieve the earlobe or other suitable tissue site from undue pressure. In one embodiment, the clip type sensor includes windows for the optical components of an oximetry sensor that allow for transmission of optical energy to or from a tissue site. The silicone lenses each comprise a translucent silicone material covering the foregoing windows.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements. In addition, the first digit of each reference number indicates the figure in which the element first appears.

FIGS. 8A-B are top views of a detector shield without and with a mounted detector, respectively;

FIGS. 13A-D are top, perspective, side and front-end views, respectively, of a clip outer jaw;

FIGS. 14A-E are perspective, top, side, bottom and front-end views, respectively, of a clip innerjaw;

FIGS. 15A-D are side, back, sectional and back perspective views, respectively, of an ear hanger;

FIGS. 16A-C are side views of an unformed, partially formed and fully formed ear hanger, respectively;

FIGS. 17A-E are views of an adhesive tab and an associated tab carrier;

FIGS. 17A-B are top and side views of a tab carrier;

FIGS. 17C-D are top and side views of an adhesive tab; and

FIG. 17E is a top view of a tab handle; and

FIGS. 18A-F are top, front perspective, side, back, rear perspective and bottom perspective views, respectively, of an ear sensor boot.

DETAILED DESCRIPTION OF THE PREFERRED EMBODIMENT

To facilitate a complete understanding of the invention, the remainder of the detailed description describes the invention with reference to the drawings, wherein like reference numbers are referenced with like numerals throughout.

Figure 1:
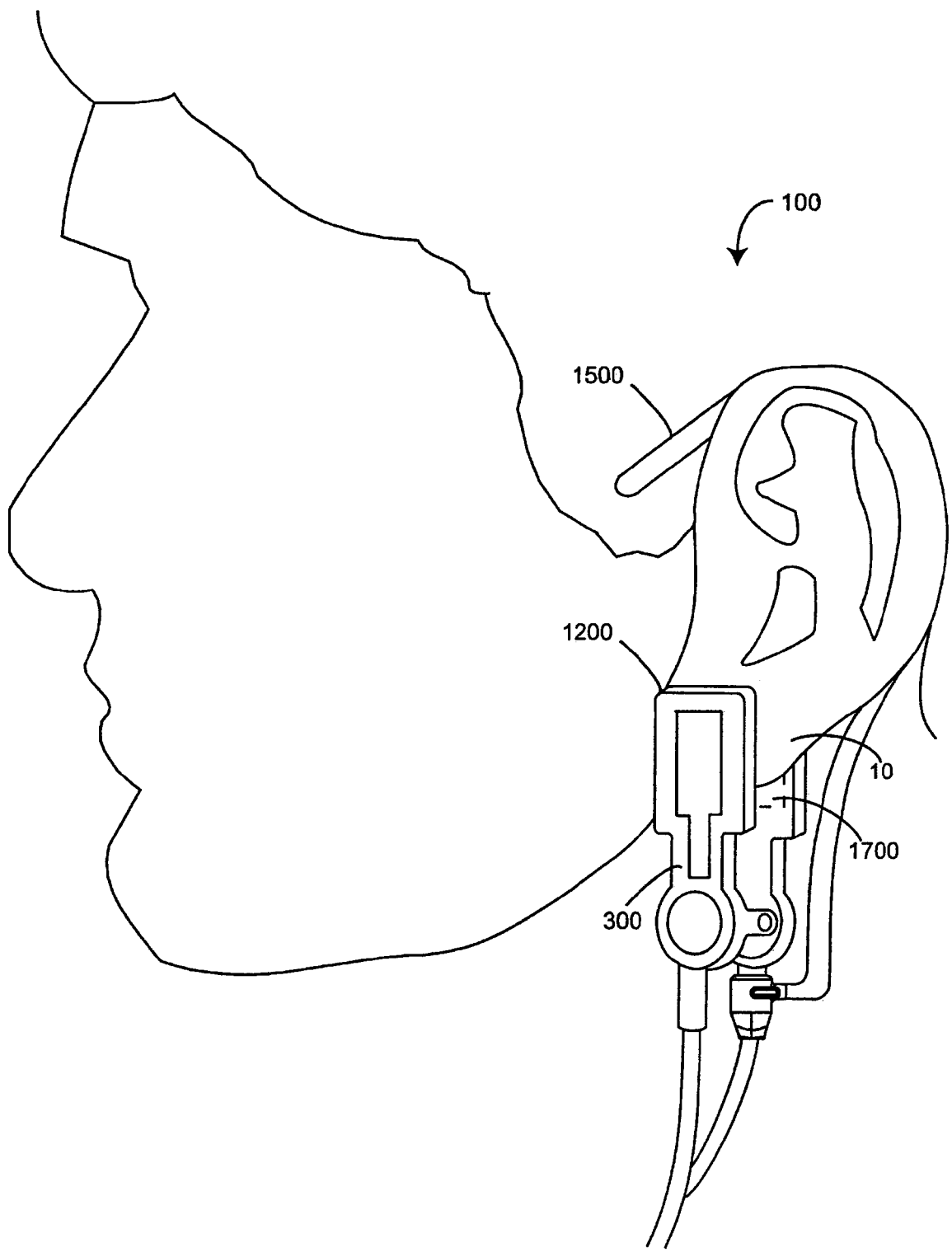
FIG. 1 is a perspective view of a pulse oximetry ear sensor attached to a patient, according to an embodiment of the invention.

FIG. 1 illustrates a pulse oximetry ear sensor assembly 100 attached to an ear monitoring site 10. The ear sensor assembly 100 includes an ear sensor 300, a replaceable clip 1200, an ear hanger 1500 and adhesive tabs 1710. The clip 1200 advantageously has a relatively low spring tension and the area of the ear sensor 300 that contacts the ear is relatively large compared with conventional ear sensors, allowing longer monitoring on the ear by reducing patient discomfort and pressure necrosis. To provide secure sensor attachment to the ear site 10, the ear sensor assembly 100 optionally utilizes an ear hanger 1500 and adhesive tabs 1710, individually or in combination, to supplement the clip 1200. The ear hanger 1500 goes around the ear, much like sports glasses, and supports the weight of the ear sensor assembly 100. The adhesive tabs 1710 may be added to the ear sensor 300 to provide adhesive attachment to the tissue site 10. Further, a clasp (not shown) may be added to a sensor cable 900 (FIG. 2) and attached to patient clothing, for example, to provide strain relief and reduce the risk that accidental cable snags might pull the ear sensor 300 off of the ear.

Figure 2:
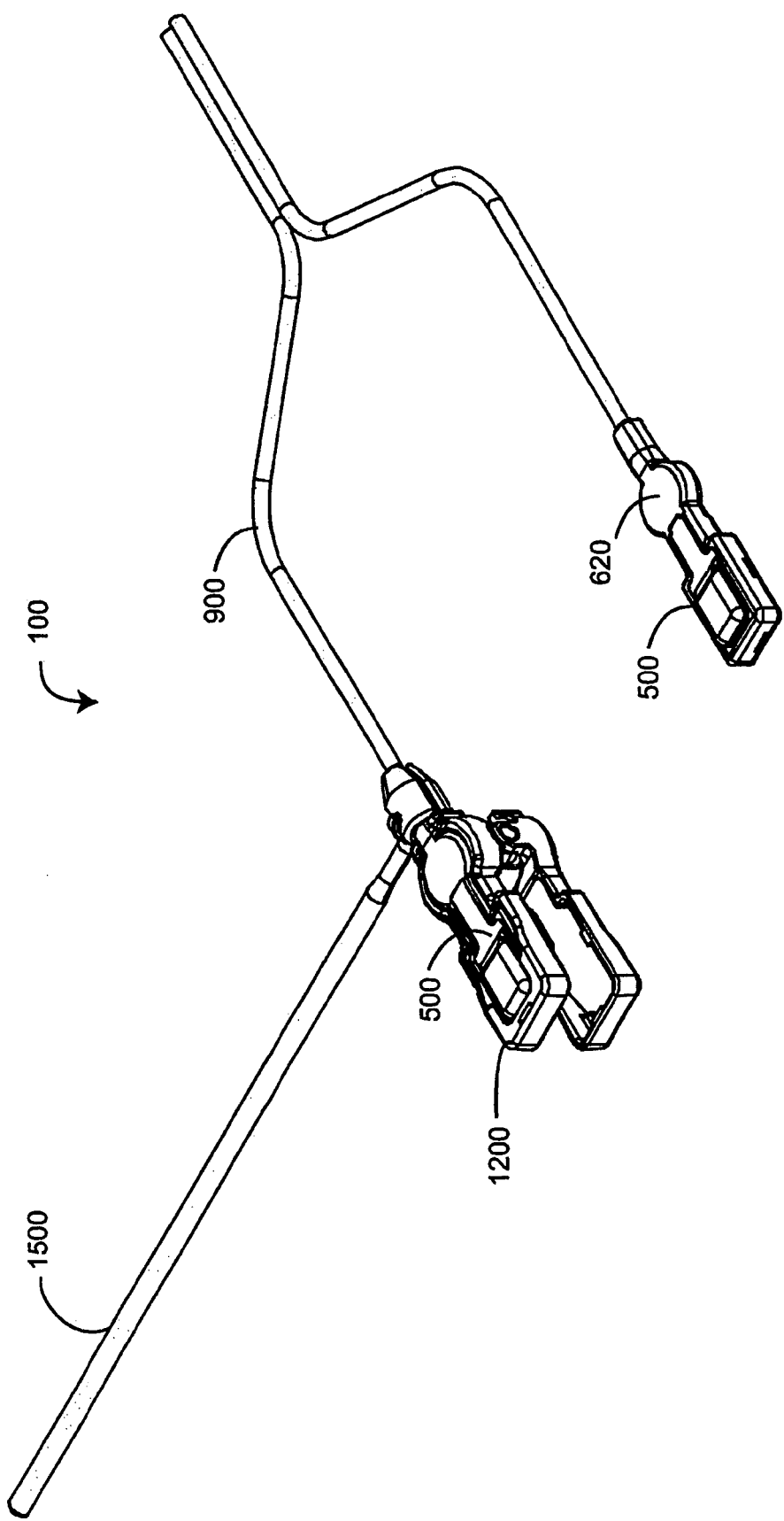
FIG. 2 is a perspective view of an ear sensor assembly.

FIG. 2 further illustrates the ear sensor assembly 100. Ear sensor pads 500 removably press-fit into the clip 1200. The clip 1200 advantageously allows inexpensive replacement of a moving part upon wear or breakage. The ear hanger 1500 removably clamps to an ear sensor cable 900. The ear hanger 1500 is advantageously constructed to be easily bent and shaped to comfortably fit various ear shapes and sizes, as described in further detail with respect to FIGS. 15-16, below. The ear hanger 1500 is provided to users either straight or preformed as shown in FIG. 16C. Additionally, FIG. 2 shows the ear sensor assembly including one or more integrated finger grips 620 as will be described in further detail with respect to FIG. 10 below.

Figure 3:
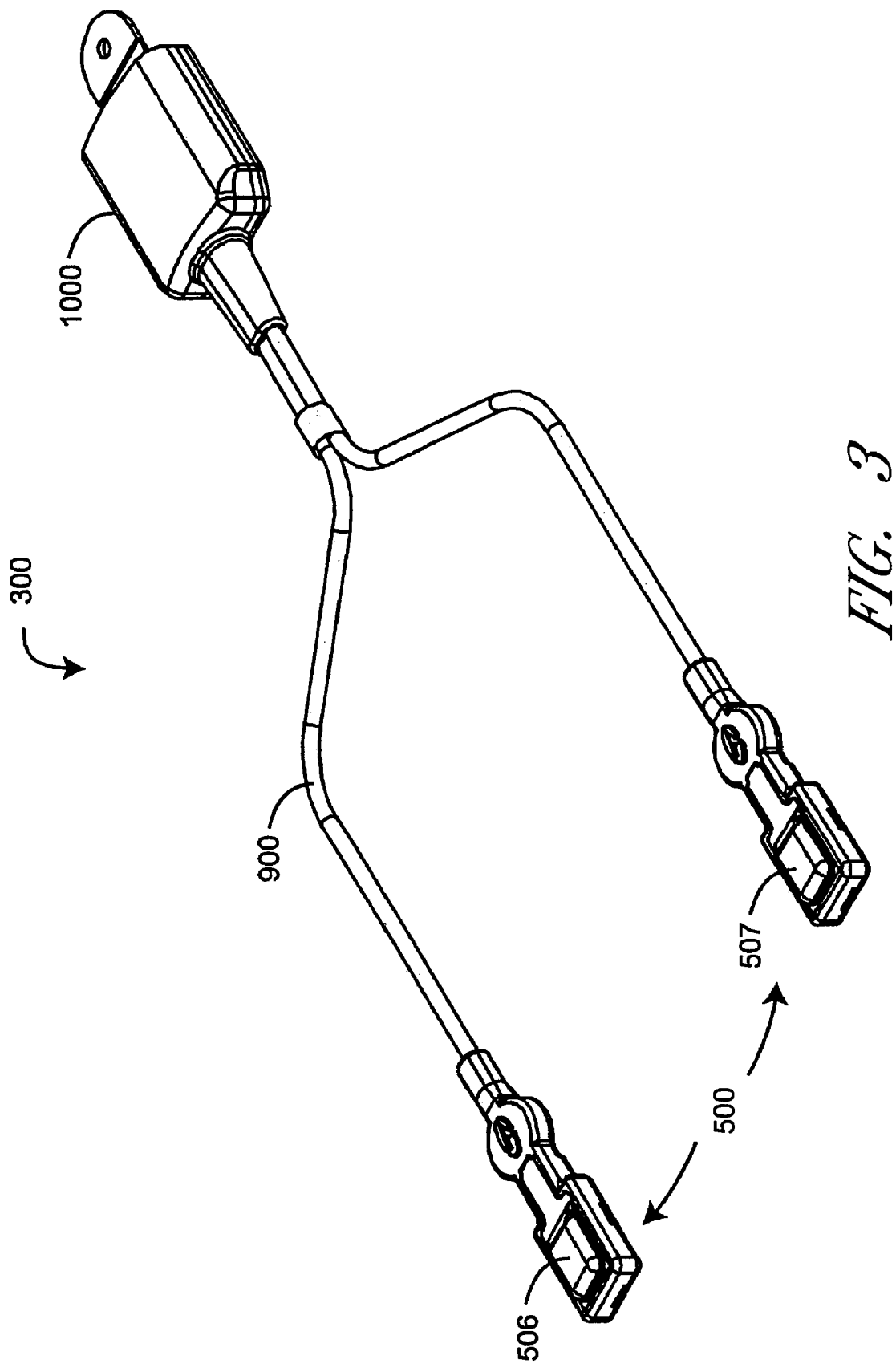
FIG. 3 is a perspective view of an ear sensor.

FIG. 3 illustrates the ear sensor 300 including the sensor pads 500, the sensor cable 900 and a modular connector 1000. The sensor pads 500 house the sensor optical components and include a detector pad 506 and an emitter pad 507. The sensor cable 900 provides a signal path between the sensor pads 500 and the modular connector 1000. The modular connector 1000 provides pinouts for a patient cable (not shown), which is used to provide communication between the ear sensor 300 and a pulse oximeter (not shown).

Figure 4:
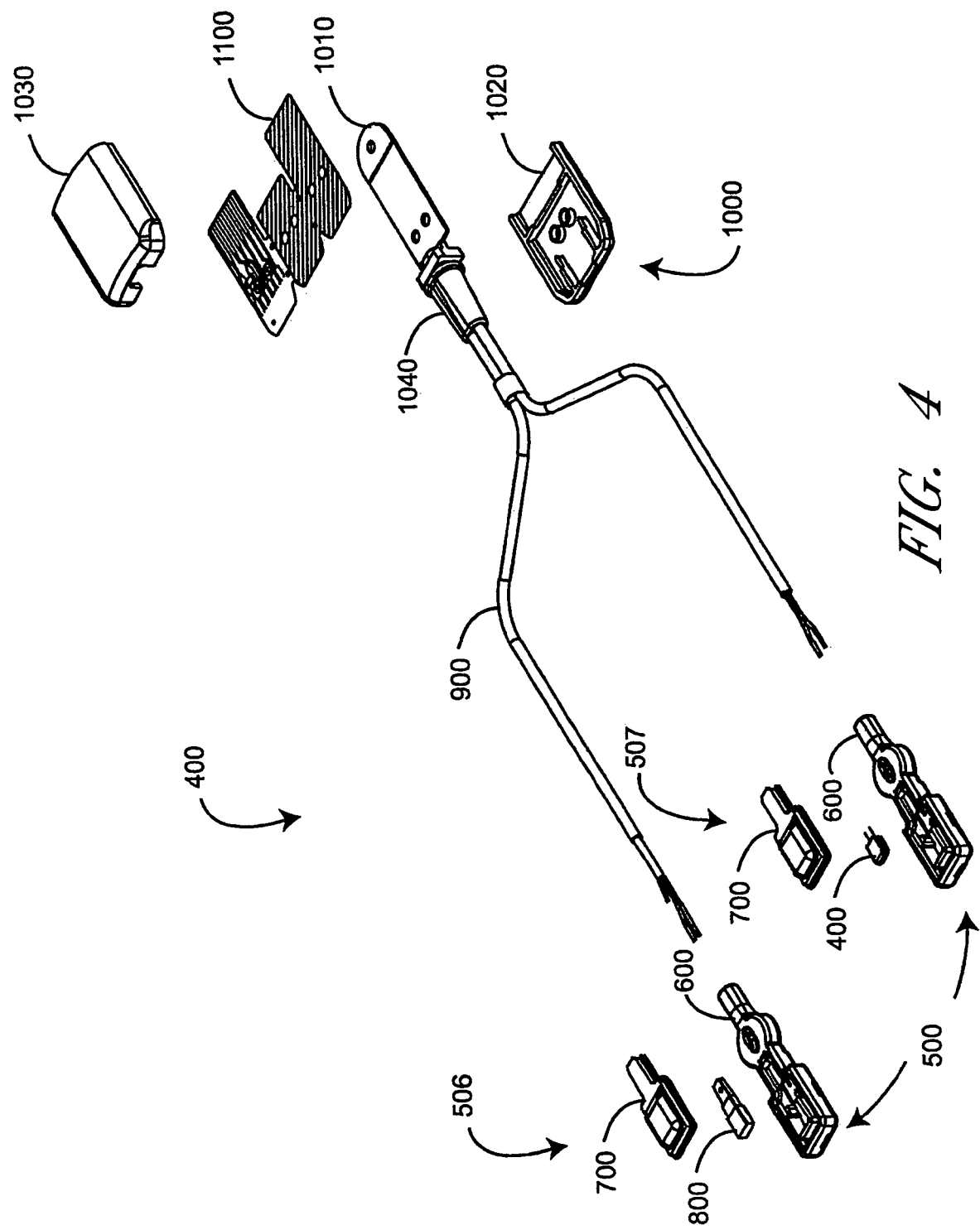
FIG. 4 is an exploded perspective view of an ear sensor.

FIG. 4 illustrates pieces of the ear sensor 300. The sensor pads 500 advantageously include a common base 600 and cover 700 for each of the detector pad 506 and the emitter pad 507. According to an embodiment used, the base 600 and cover 700 reduces or even minimizes the number of unique parts for the ear sensor 300. The detector pad 506 houses a shielded detector assembly 800. The emitter pad 507 houses an emitter 400. The modular connector 1000 includes a connector flex circuit 1100 installed onto a tab 1010 and enclosed between a bottom cover 1020 and a top cover 1030 that clasp a bend relief 1040.

Figure 5B:
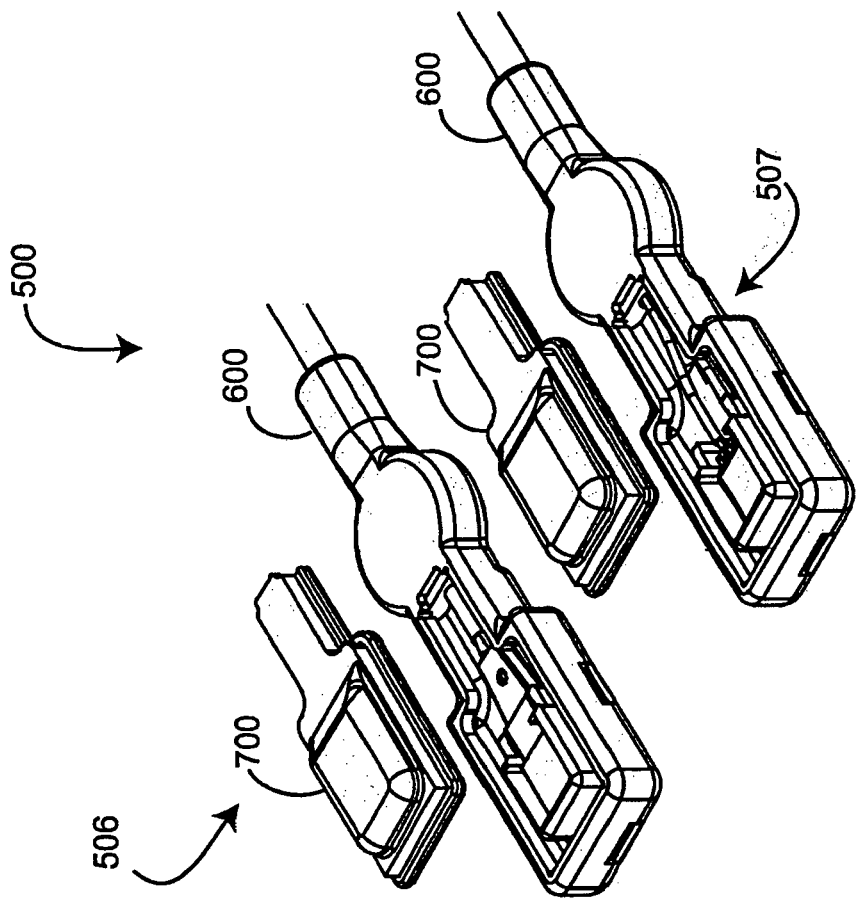
FIGS. 5A-B are top and perspective views, respectively, of ear sensor pad assemblies.
Figure 5A:
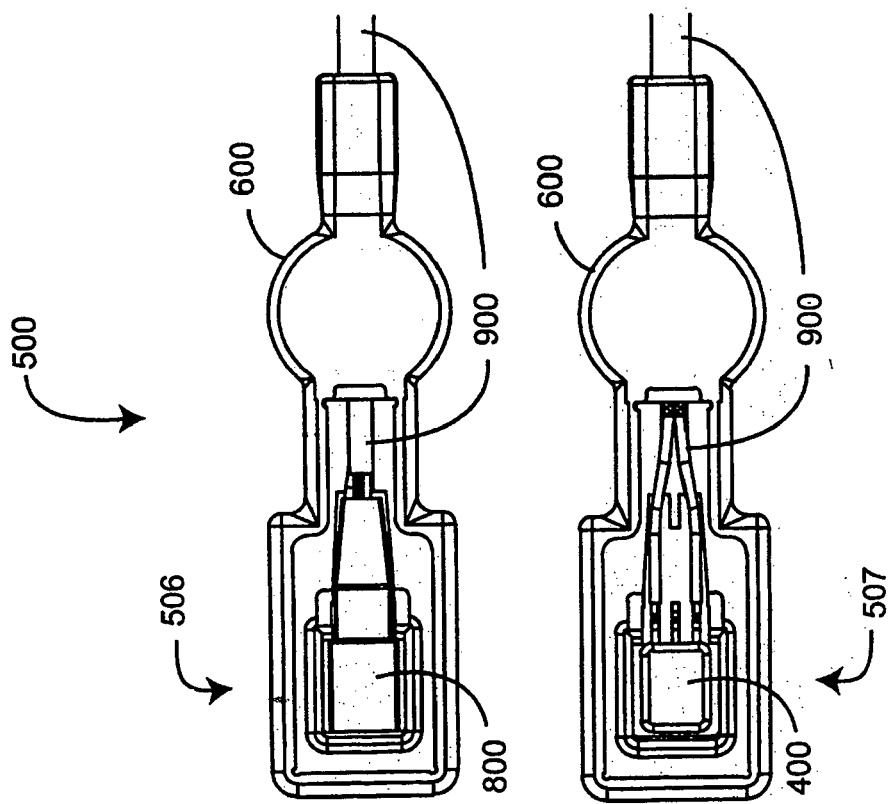

FIGS. 5A-B further illustrate exemplary embodiments of the detector and emitter pads 500. As shown in FIG. 5A, both the detector (not visible) within the shielded detector assembly 800 and the emitter 400 are connected to the sensor cable 900 after the cable is inserted into the respective bases 600. As shown in FIG. 5B, the cover 700 is secured in place onto the base 600 so as to enclose, and in an embodiment, seal the shielded detector assembly 800 and emitter 400 in their respective housings.

Figure 6B:
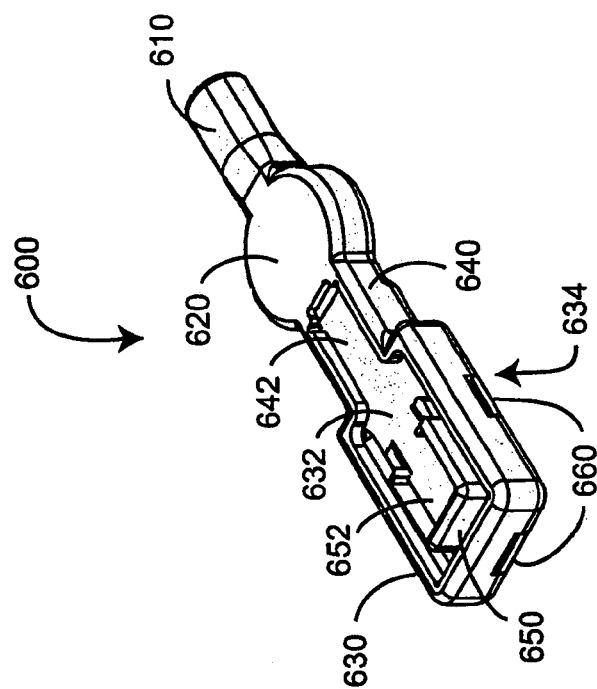
FIGS. 6A-B are top and perspective views, respectively of a pad base.
Figure 6A:
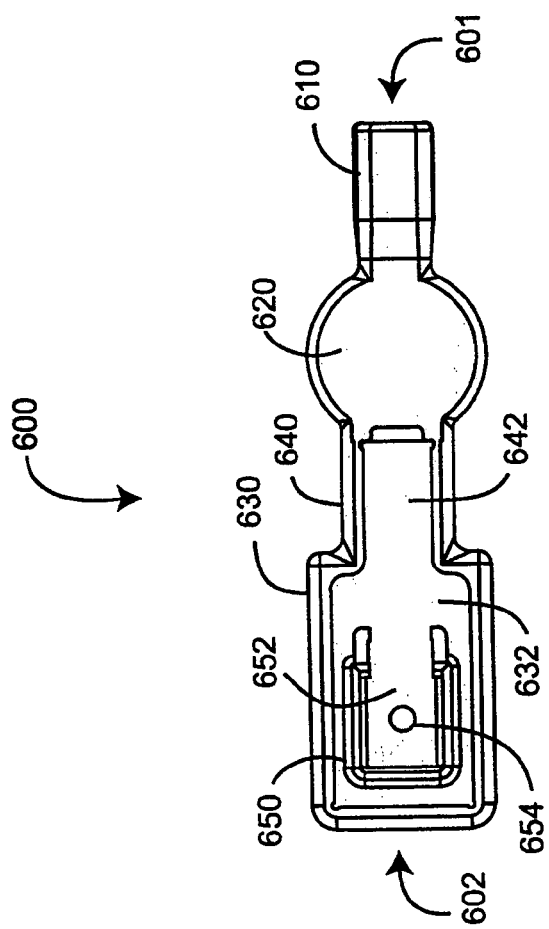
Figure 9:
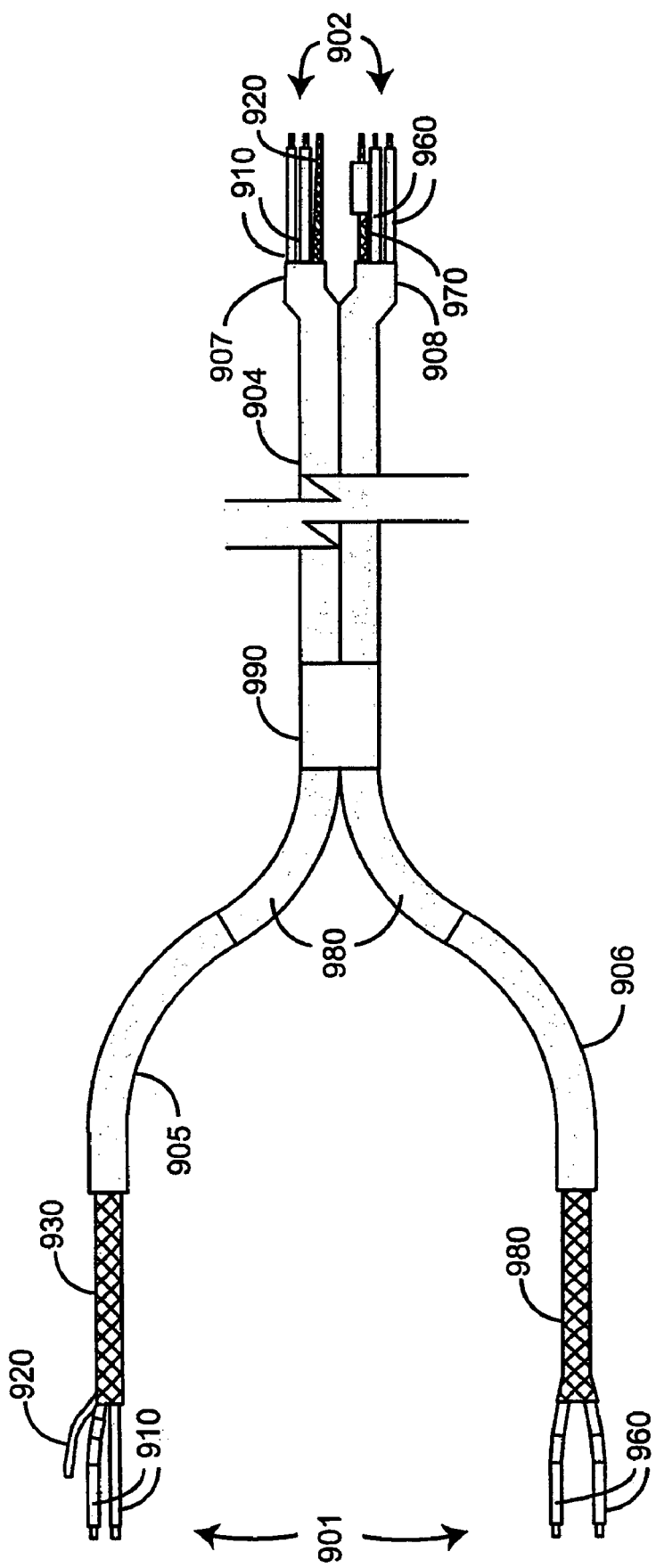
FIG. 9 is a top view of an ear sensor cable.
Figure 12B:
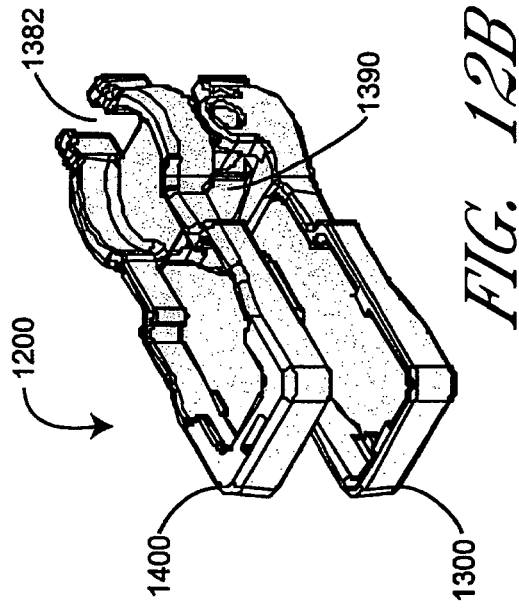
FIGS. 12A-C are exploded, front perspective and back perspective views, respectively, of a sensor clip.
Figure 12C:
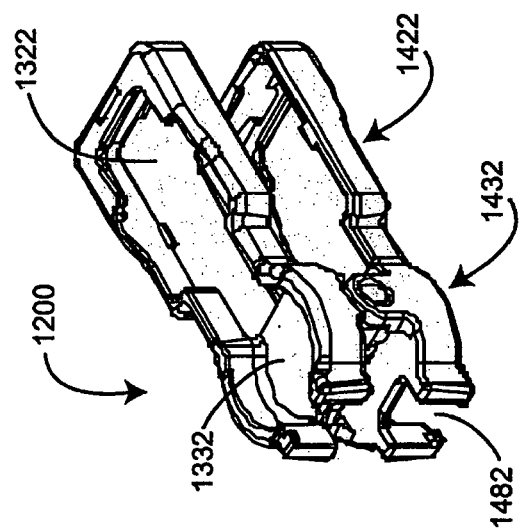
Figure 12A:
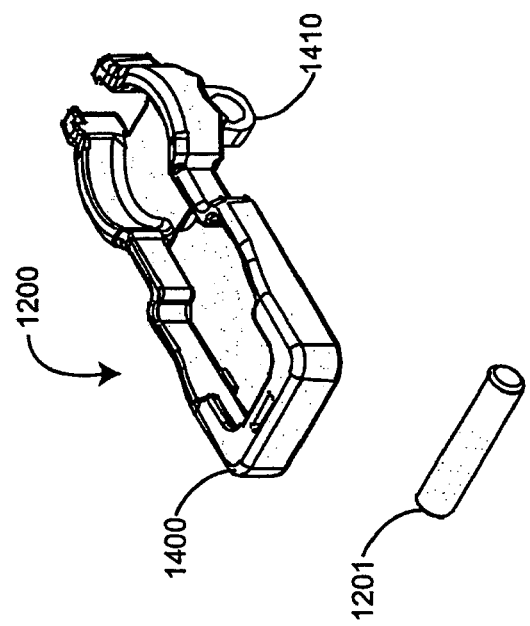
Figure 18F:
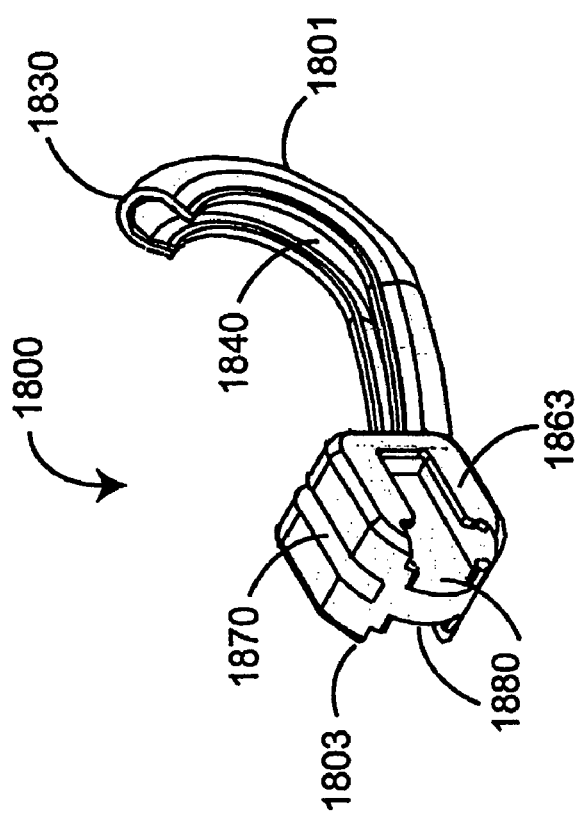
Figure 18E:
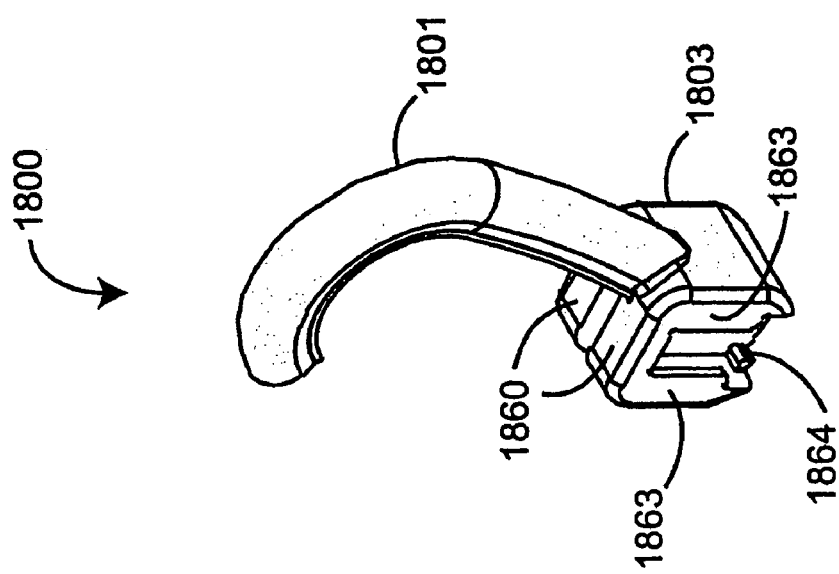
Figure 19A:
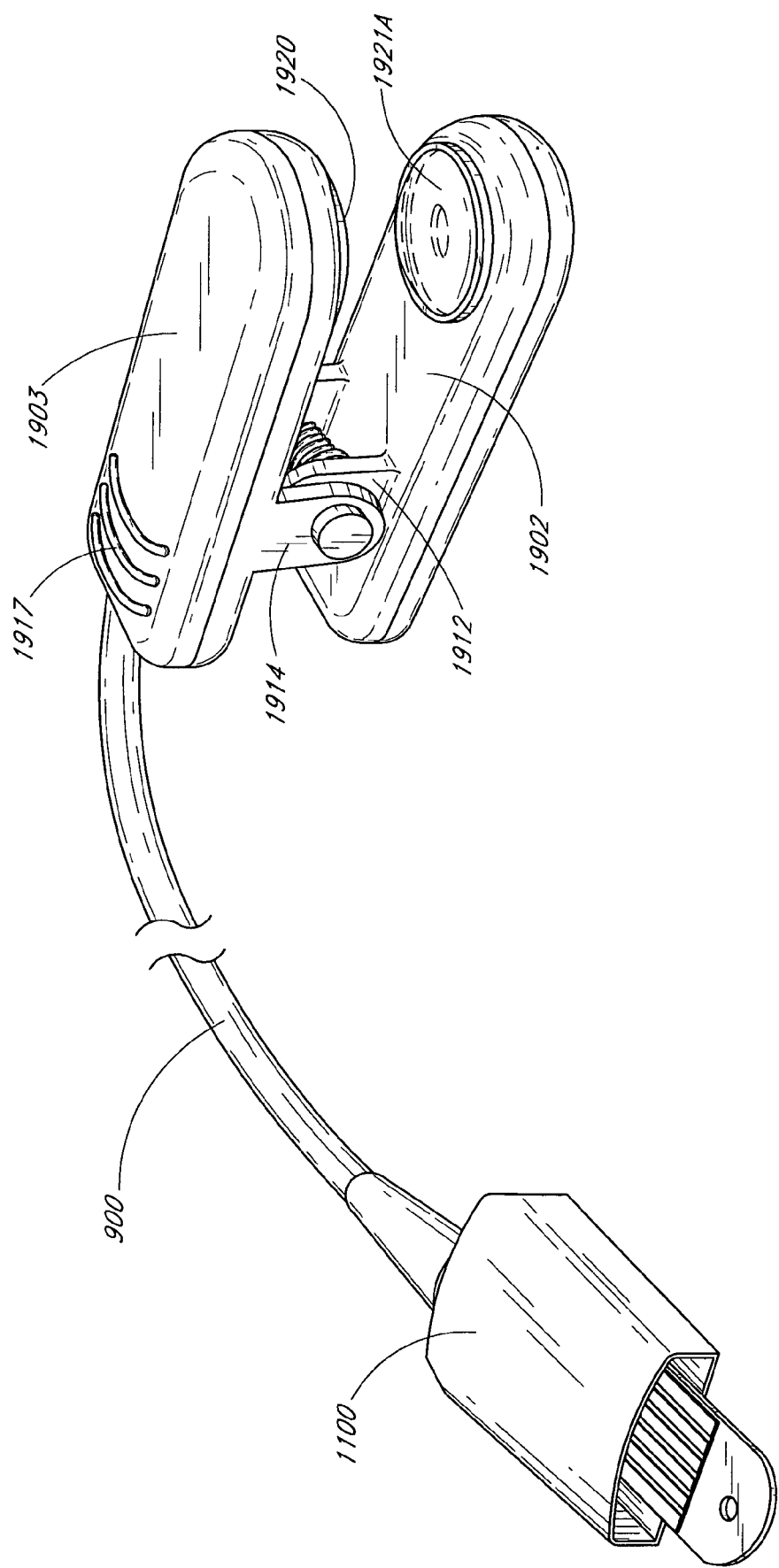
FIGS. 19A-D are assembled front perspective, exploded bottom, exploded top, and rear perspective views, respectively, of an ear sensor clip with one or more silicone lenses.
Figure 19B:
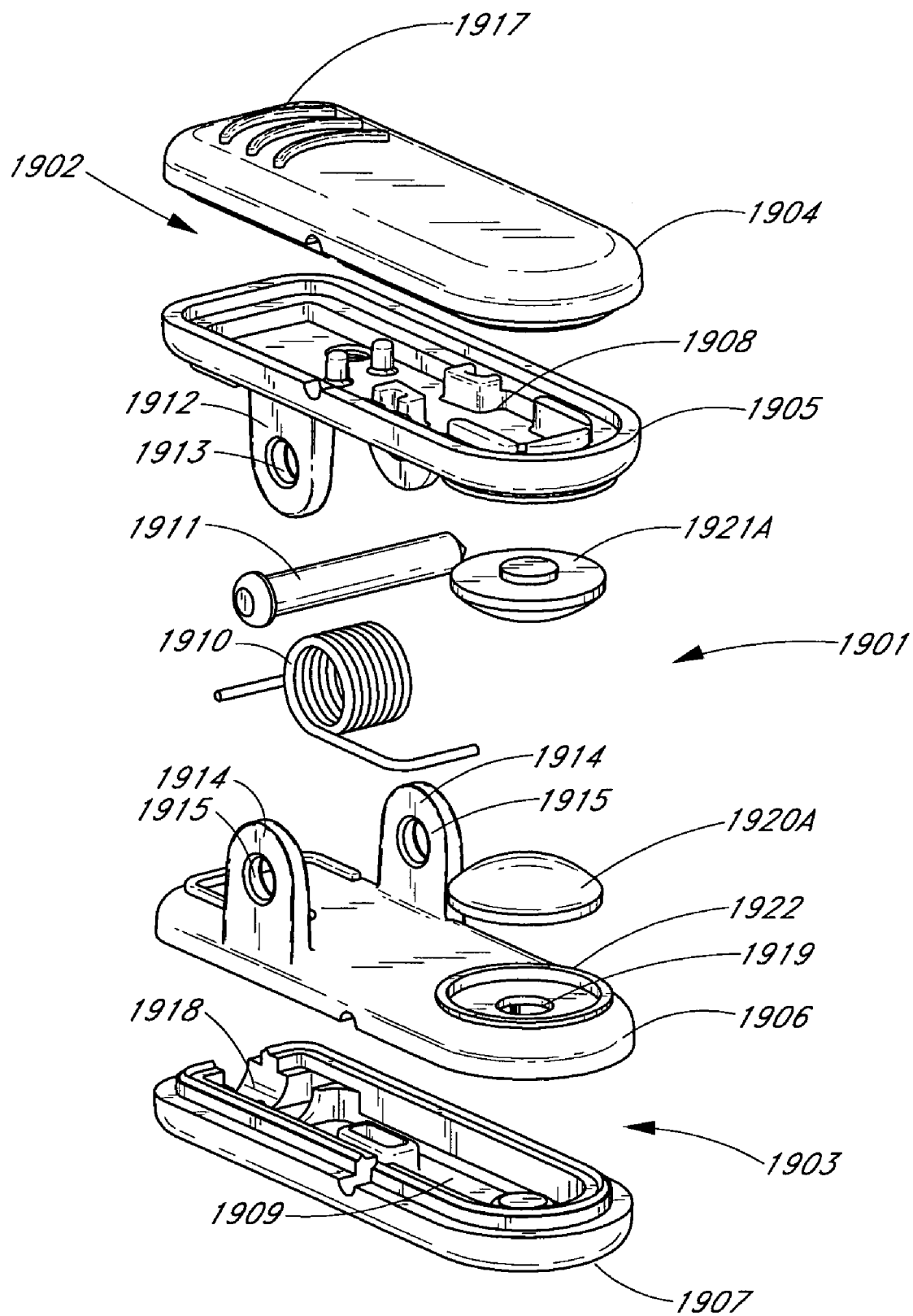
Figure 19C:
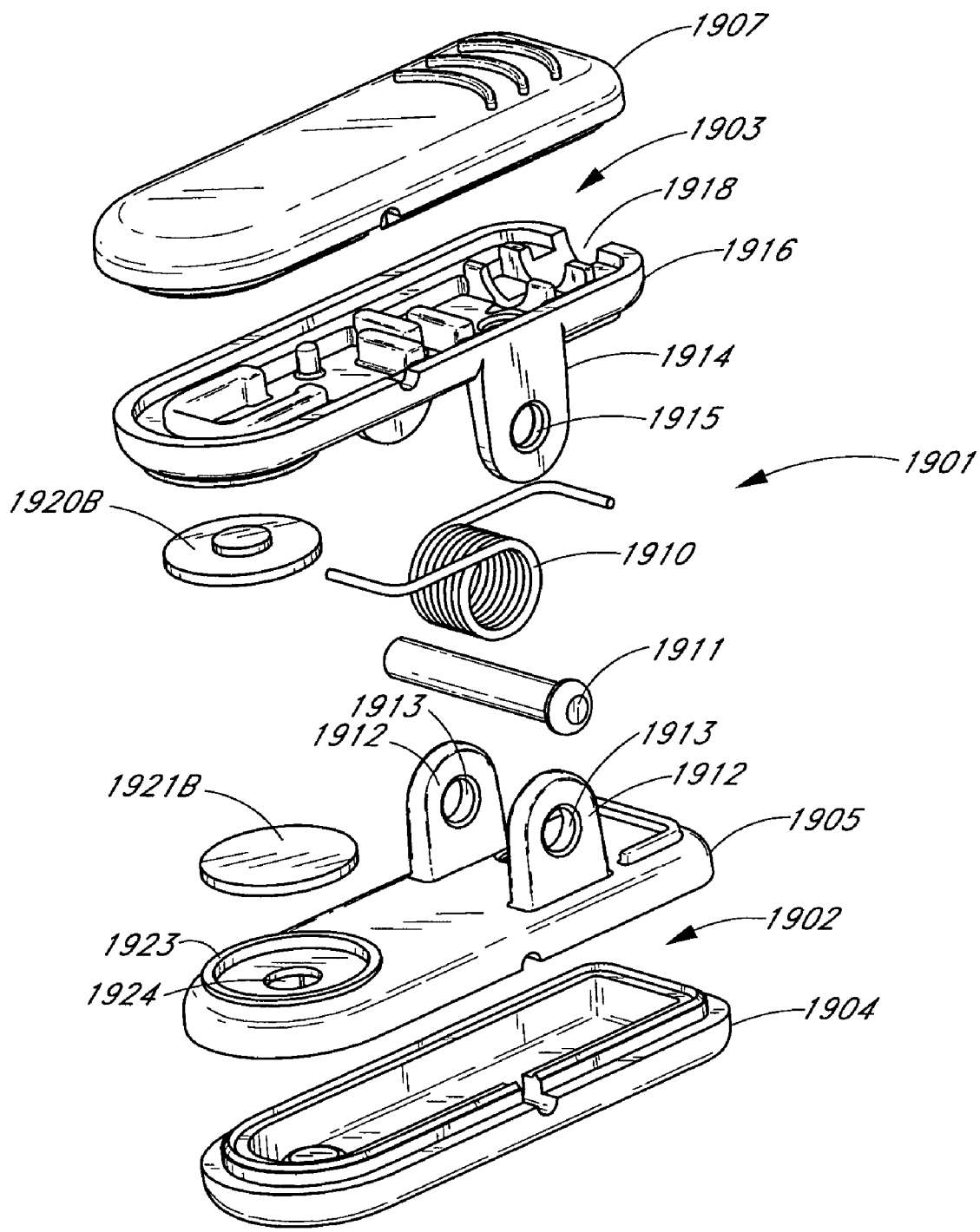
Figure 19D:
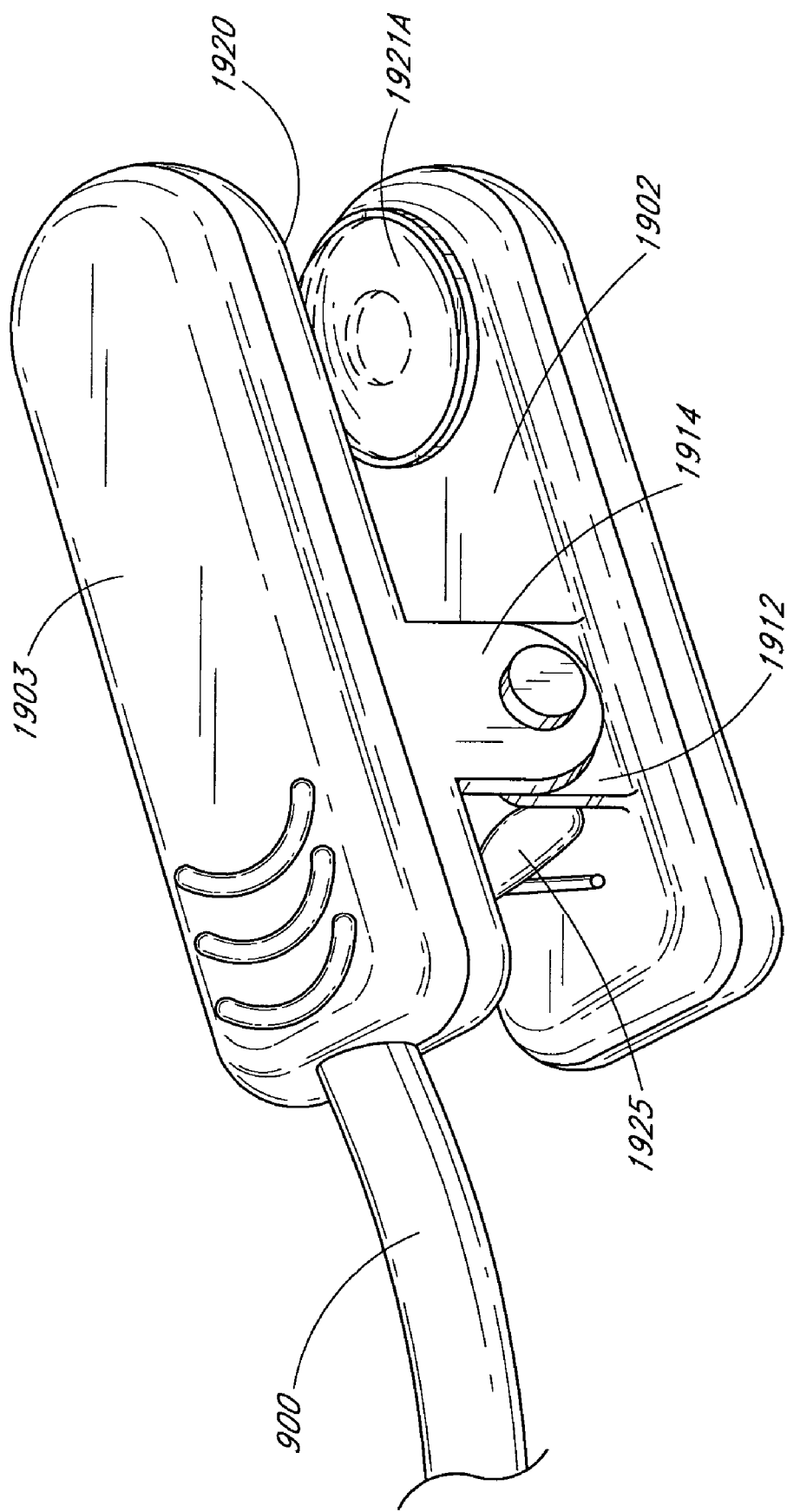

FIGS. 6A-B illustrate a base 600 having a bend relief 610, the integrated finger grip 620, a head 630 and a head extension 640. The base 600 has a cable end 601 and a head end 602. The bend relief 610 extends between the cable end 601 and the finger grip 620 and is configured to accept one end of the sensor cable 900 (FIG. 9). The bend relief 610 is adapted to reduce bending stress on the sensor cable 900 (FIG. 9). The finger grip 620 extends between the bend relief 610 and the head extension 640 and provides a finger pressing surface so as to open the clip 1200 (FIGS. 12A-C). In one embodiment, the finger grip 620 provides a generally round, planar surface that may be comprised of a generally pliable material.

As shown in FIGS. 6A-B, the head 630 extends between the head end 602 and the head extension 640, opposite the head extension 640 from the finger grip 620. The head 630 has an open face 632 and an opposite, generally planar pad face 634. The pad face 634 provides a generally planar contact surface for a tissue site. Advantageously, the pad face 634 has a relatively large area to minimize the force on a tissue site. In one embodiment, the area of the pad face 634 is in the range of about 0.225 sq. in. to about 0.325 sq. in. In a particular embodiment, the pad face 634 is generally rectangular. In a specific embodiment, the pad face 634 has dimensions of about 0.69 in. by about 0.45 in. However, a skilled artisan will recognize from the disclosure herein that the pad face 634 may be sized to take into account a wide variety of parameters, including for example, tissue site size, component size, necrosis, patient comfort, combinations of the same or the like.

Figure 7:
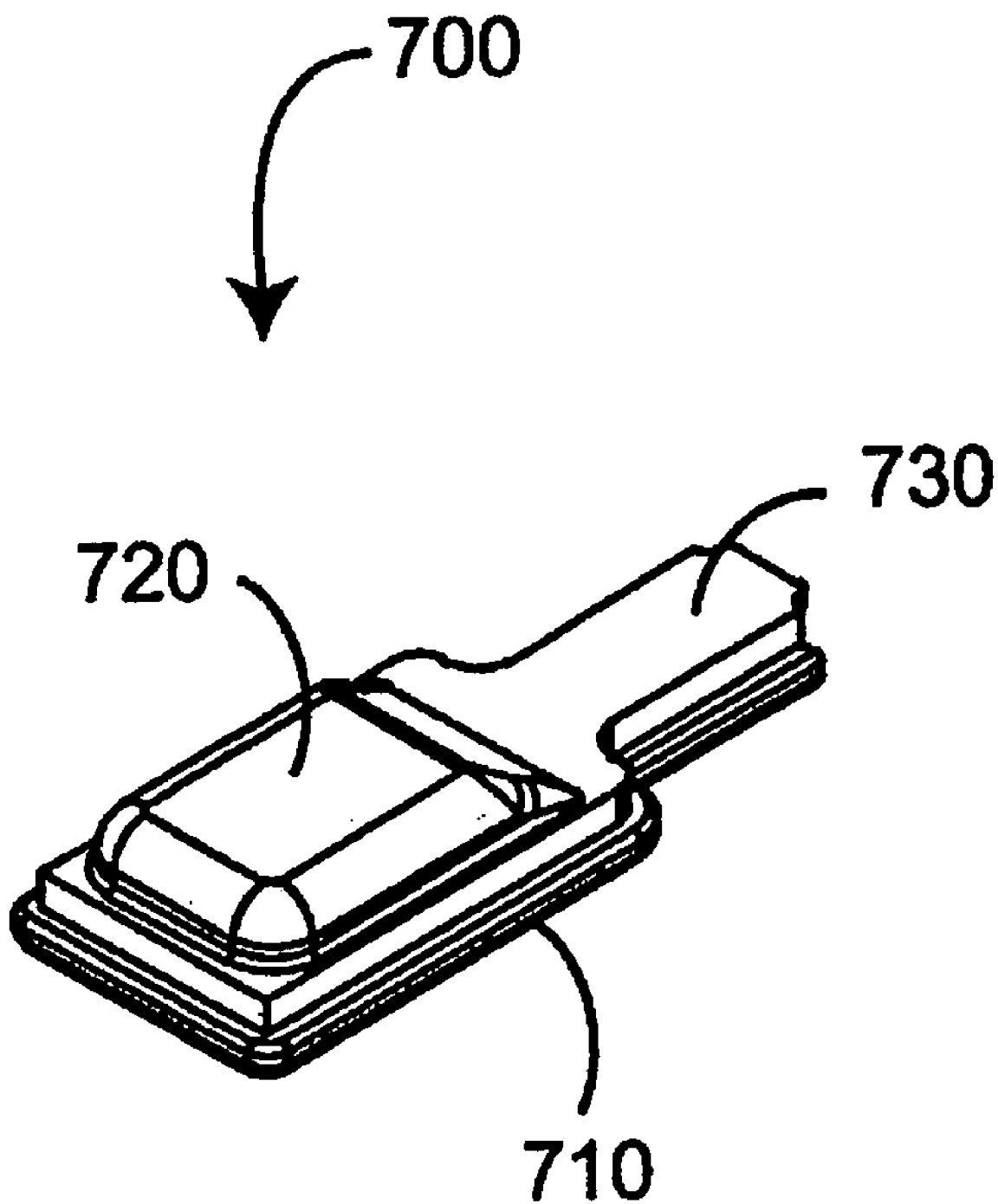
FIG. 7 is a perspective view of a pad cover.

Also shown in FIGS. 6A-B, the open face 632 is configured to accept an optical component. In one embodiment, the open face 632 has a raised wall 650 defining a component cavity 652 configured to accept and retain either an emitter 400 (FIG. 4) or a detector assembly 800 (FIG. 4). The open face 632 also defines a window 654 that provides an aperture for transmission of optical energy to or from a tissue site. In one embodiment, the window 654 is filled with a translucent silicone material as will be further described with reference to FIG. 19. The extension 640 extends between the finger grip 620 and the head 630 and provides a channel 642 for the sensor cable 900 (FIG. 9). In one embodiment, the open face 632 is closed and sealed with the pad cover 700 (FIG. 7). The base 600 has slots 660 disposed along the base edges. The slots 660 are configured to mate with corresponding clip tabs 1326 (FIGS. 13A-D), 1426 (FIGS. 14A-E) so as to retain the pads 500 (FIGS. 5A-B) within the clip 1200 (FIGS. 12A-C), as described with respect to FIGS. 12A-C, below.

FIG. 7 illustrates a pad cover 700 having a platform 710, a raised cap 720 and an extension 730. The cover 700 can be configured to close and seal the base 600 (FIGS. 6A-B), as described with respect to FIG. 5B. In particular, the platform 710 corresponds to the open face 632 and covers an optical component. The raised cap 720 accommodates an optical component accordingly. The extension 730 corresponds to the channel 642 (FIGS. 6A-B) and covers the sensor cable leads. Both the base 600 (FIGS. 6A-B) and the cover 700 can be injection molded of a pliant material. In one embodiment, the material is a medical grade thermoplastic elastomer, such as AES Santoprene, #281-45. In a particular embodiment, the base 600 (FIGS. 6A-B) is constructed of a reflective material so as to advantageously reflect scattered light back into the tissue site, while the cover 700 is constructed of an absorbent material so as to block ambient light for noise reduction at the detector.

FIGS. 8A-B illustrate the shielded detector assembly 800, having a shield 801 and a detector 802. The shield 801 has a back shield 810, a front shield 820 having a grid 822, a detector lead shield 830 and a cable lead shield 840. The detector 802 is placed on the shield 801 so that the front, light-receiving face (not visible) is proximate to and aligned with the grid 822. The sensor cable 900 is attached to the detector 802 so that the detector cable leads 910 are electrically connected to the detector leads 803 and the detector cable shield lead 920 is electrically connected to the cable lead shield 840. The shield 801 is then folded so that the back shield 810 is placed over the back face of the detector 802, the sides of the front shield 820 are placed over the detector sides, the detector lead shield 830 is folded over the detector leads 803 and the cable lead shield 840 is folded over the cable leads 920.

FIG. 9 illustrates a sensor cable 900 having a sensor end 901, a connector end 902, a cable midsection 904, a detector cable 905 and a emitter cable 906. Both the detector cable 905 and emitter cable 906 extend between the sensor end 901 and the connector end 902. The detector cable 905 and emitter cable 906 are joined throughout the cable midsection 904. The detector cable 905 and emitter cable 906 are separated at a Y-section 980 proximate the sensor end 901. A binder 990, such as a shrink-wrap insulator or an over mold section, binds the cable 900 between the Y-section 980 and the midsection 904 to prevent the Y-section 980 from extending into the midsection 904 by inadvertent separation of the detector cable 905 and emitter cable 906. The detector cable 905 has detector cable leads 910 and a detector cable shield 930 that has a shield lead 920 formed from the shield 930 at both the sensor end 901 and the connector end 902. The emitter cable 906 has emitter cable leads 960 and an emitter cable shield 980 that has a shield lead 970 formed from the shield 980 at the connector end 902. An insulator 972 on the emitter cable shield lead 970 prevents electrical contact with the detector cable shield lead 920.

Figure 10B:
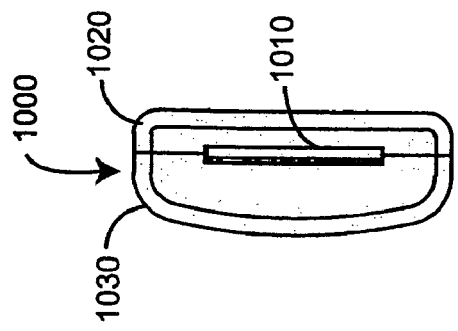
FIGS. 10A-C are top enclosed, end enclosed, and bottom unenclosed views of a modular plug.
Figure 10A:
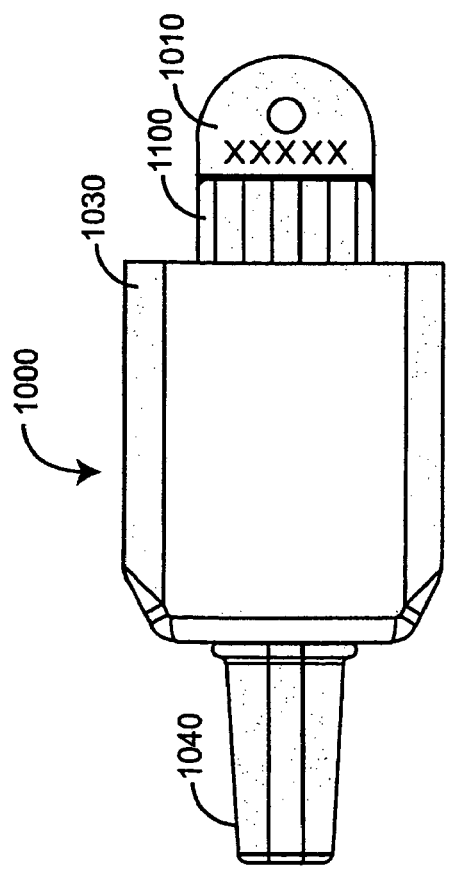
Figure 10C:
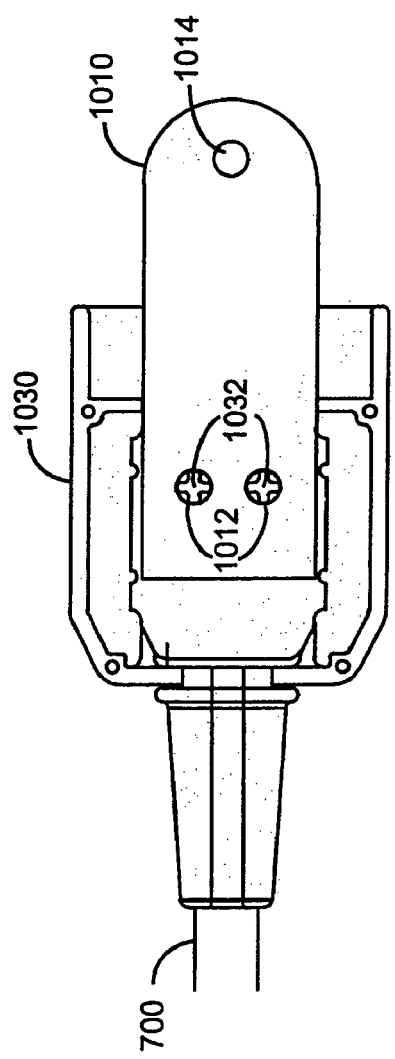

FIGS. 10A-C illustrate the cable connector 1000 having a tab 1010, a lower shell 1020, an upper shell 1030 and a bend relief 1040. As shown in FIG. 10A, the tab 1010 supports a flexible circuit assembly 1100, which provides connector pinouts and connections to the sensor cable 900, as described with respect to FIGS. 11A-B, below. The lower shell 1020 and upper shell 1030 are mating halves of the connector body, which provides a grip for connecting to a patient cable, protects the flexible circuit connections and retains the bend relief 1040. The bend relief 1040 prevents the sensor cable 900 from bending a sharp angles at the boundary of the connector body 1020, 1030. As shown in FIG. 10C, the tab 1010 has a catch 1014 that provides a locking mechanism for a patient cable connector, such as described in U.S. Pat. No. 6,152,754 entitled "Circuit Board Based Cable Connector," assigned to Masimo Corporation, Irvine, Calif. and incorporated by reference herein. The tab 1010 also has apertures 1012 that accept corresponding posts 1032 of the upper shell 1030. The posts 1032 fit into corresponding standoffs (not shown) of the lower shell 1020 so that the tab is held in position between the lower shell 1020 and upper shell 1030.

Figures 11A, 11B:
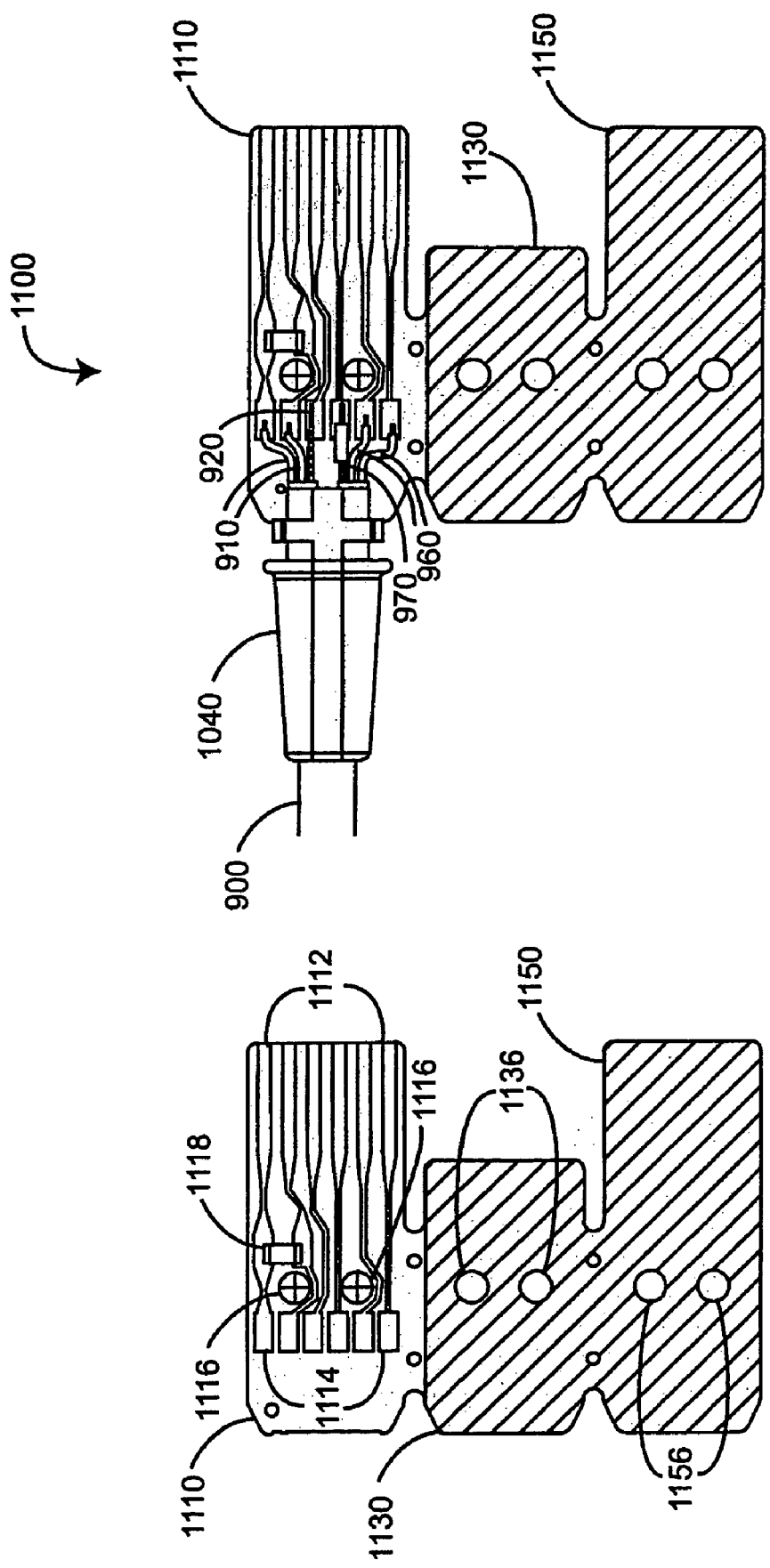
FIGS. 11A-B are top views of a connector flex circuit, with and without an attached sensor cable, respectively.

FIGS. 11A-B illustrate a self-shielding flexible circuit assembly 1100 having a printed circuit 1110, a top shield 1130 and a bottom shield 1150. As shown in FIG. 11A, the printed circuit 1110 has pinouts 1112, lead pads 1114, apertures 1116 and an information element 1118. The pinouts 1112 are electrically connected to corresponding ones of the lead pads 1114 and provide the connection to a mating patient cable connector. The apertures 1116 align with upper shell posts 1032 (FIG. 10C). The information element 1118 provides sensor information, such as sensor type, to a compatible pulse oximeter instrument connected to the ear sensor 300 (FIG. 3) via a patient cable (not shown). An information element is described in U.S. Pat. No. 6,011,986 entitled "Manual And Automatic Probe Calibration," assigned to Masimo Corporation, Irvine, Calif. and incorporated by referenced herein.

As shown in FIG. 1B, the sensor cable 900 is integrated with the flexible circuit assembly 1100 with the cable leads 910, 920, 960, 970 attached and electrically connected to corresponding ones of the lead pads 1114, such as with a soldered connection. After the sensor cable 900 is attached to the printed circuit 1110, the top shield 1130 is folded over the printed circuit traces 1112, 1114 and the bottom shield 1150 is wrapped around the printed circuit 1110 and folded over the bottom of the printed circuit 1110. In this manner, the connections, in particular the detector leads 910, are EMI shielded and physically protected. The top shield 1130 and bottom shield 1150 are folded so that top shield apertures 1136 and bottom shield apertures 1156 align with the printed circuit apertures 1116. The folded flexible circuit assembly 1100 is attached to the tab 1010 (FIGS. 10A-C) with an adhesive, such as PSA, and mounted within the connector shells 1020, 1030 (FIG. 10B), as described above.

FIGS. 12A-C illustrate a removable sensor clip 1200. As shown in FIG. 12A, the removable clip 1200 has an outer jaw 1300, an inner jaw 1400, a hinge pin 1201, and a hinge spring 1202. The outer jaw 1300 has an outer hinge support 1310, and the inner jaw 1400 has an inner hinge support 1410. The clip 1200 is assembled with the hinge supports 1310, 1410 aligned, the spring 1202 between the hinge supports 1310, 1410, and the pin 1201 inserted through the hinge supports 1310, 1410 and the spring 1202 so as to rotatably attach the jaws 1300, 1400 at their respective hinge supports 1310, 1410. The spring 1202 urges the jaws to a closed position in which the sensor pads 500 (FIGS. 5A-B) are held against an earlobe or other suitable tissue site.

The spring 1202 is advantageously designed so that the force the jaws 1300, 1400 exert on a tissue site is relatively small. In an embodiment, the ear sensor assembly 300 (FIG. 3) utilizes various attachment mechanisms to supplement or supplant the jaw force in maintaining sensor attachment to the tissue site, including an ear hanger 1500 (FIGS. 15A-D), ear boot 1800 (FIGS. 18A-F), adhesive tabs 1710 (FIG. 17C), and/or silicone lenses (FIGS. 19A-D) described below. In a preferred embodiment, the force of the jaws 1300, 1400 on a tissue site is in the range of about 90 gram force to about 140 gram force. In a more preferred embodiment, the jaw force is in the range of about 115 gram force to about 130 gram force. In a most preferred embodiment, the jaw force is about 116 gram force. However, an artisan will recognize from the disclosure herein that a wide number of ranges can be implemented for the jaw force. For example a clip used on trauma or other potentially active patients or difficult tissue sites may use more or less force.

As shown in FIGS. 12B-C, the assembled clip 1200 has opposing head holders 1322, 1422 that removably retain the head portions 630 (FIGS. 6A-B) of the sensor pads 500 (FIGS. 5A-B). The assembled clip 1200 also has opposing grip holders 1332, 1432 that removably retain the finger grips 620 (FIGS. 6A-B). The finger grips 620 (FIGS. 6A-B) are squeezed so as to move the jaws 1300, 1400 to an open position in which the pads 500 (FIGS. 5A-B) are separated for positioning the ear sensor 300 (FIG. 3) on a tissue site or for removal of the ear sensor 300 (FIG. 3) from a tissue site. End slots 1382, 1482 removably retain the pad bend reliefs 610 (FIGS. 6A-B). A jaw stop 1390 advantageously prevents the jaws 1300, 1400 from closing to the extent that the pad faces 634 (FIGS. 6A-B) touch. In this manner, adhesive tabs 1710 (FIG. 17C) can be applied to the pad faces 634 (FIGS. 6A-B) to assist in holding the ear sensor 300 (FIG. 3) to an ear tissue site, without having the adhesive tabs 1710 (FIG. 17C) adhere to each other.

FIGS. 13A-D illustrate a clip outer jaw 1300 having a back end 1301, a front end 1303, a top side 1306 and a bottom side 1308. The outer jaw 1300 has a pair of hinge supports 1310, a head holder 1320 proximate the front end 1303, a grip holder 1330 extending from the back end 1301, a middle 1350 between and adjoining both the head holder 1320 and grip holder 1330, a bend relief holder 1380 at the back end 1301 and adjoining the grip holder 1330, and a jaw stop 1390. The hinge supports 1310 each extend from the bottom side 1308 at the grip holder 1330, generally perpendicular to the plane of the head holder 1320 and generally aligned with the grip holder walls 1331. The hinge supports 1310 each define a hinge aperture 1312 sized to accept and retain the hinge pin 1201 (FIG. 12A).

As shown in FIGS. 13A-D, the head holder 1320 has walls 1321 that extend from the top side 1306 to the bottom side 1308 around the periphery of the jaw 1300 so as to define a head holder interior 1322. A lip 1324 extends from the front end 1303 along the top side 1306 partially into the head holder interior 1322. Tabs 1326 extend from the walls 1321 partially into the interior 1322 of the head holder 1320. These tabs 1326 mate with corresponding base slots 660 (FIG. 6B). The head holder 1320 is configured to securely but removably retain a pad head 630 (FIGS. 6A-B). The grip holder 1330 has walls 1331 that extend from the top side 1306 to the bottom side 1308 around the periphery of the jaw 1300 so as to define a grip holder interior 1332. A shelf 1334 is disposed along the bottom side 1308 within the grip holder interior 1332. The grip holder 1330 is configured to securely but removably retain a finger grip 620 (FIGS. 6A-B).

Also shown in FIGS. 13A-D, the middle 1350 has walls 1351 that extend from the top side 1306 to the bottom side 1308 along the periphery of the jaw so as to connect the head holder walls 1321 and the grip holder walls 1331, the middle walls 1351 being closer together than the head holder walls 1321 or the grip holder walls 1331. The bend relief holder 1380 has walls 1381 that extend from the back end 1301 so as to define a bend relief slot 1382. The bend relief slot 1382 is configured to securely but removably retain the bend relief 610 (FIGS. 6A-B).

Further shown in FIGS. 13A-D, the jaw stop 1390 extends from the grip holder 1330 of the outer jaw 1300 along the bottom side 1308 proximate the middle 1350 generally normally from the jaw plane. The jaw stop 1390 is configured to contact a corresponding portion of the inner jaw 1400 so as to prevent the outer jaw 1300 and inner jaw 1400 from closing to the extent that installed sensor pads 500 (FIGS. 5A-B) would touch. In particular, the jaw stop 1390 advantageously prevents mutual contact and adhesion between adhesive pads 1710 (FIG. 17C) attached to the sensor pads 500 (FIGS. 5A-B).

FIGS. 14A-E illustrate a clip inner jaw 1400 having hinge supports 1410, a head holder 1420, a grip holder 1430, a middle 1450 and a bend relief holder 1480 as described with respect to FIGS. 13A-D, above. In one embodiment, the clip jaws 1300 (FIGS. 13A-D), 1400 are injection molded with an ABS/polycarbonate blend, such as GE Gycoloy #6200.

As shown in FIGS. 2, 6 and 12-14, sensor pads 500 are installed into a clip 1200 by inserting the heads 630 within the holder interiors 1322, 1422 underneath the lips 1324, 1424 and until the heads 630 are over the holder interiors 1322, 1422. The heads 630 are then pressed into the holder interiors 1322, 1422, the finger grips 620 are pressed into the grip holders 1330, 1430 and the bend reliefs 610 are pressed into the bend relief holders 1382, 1482. The pads 500 can be removed in a corresponding manner by lifting the bend reliefs 610 from the bend relief holders 1382, 1482 so that the bend relief 610, grip 620 and head 630 are released. The sensor pads 500 can then be pulled from underneath the lips 1324, 1424.

FIGS. 15A-D illustrate an ear hanger 1500. As shown in FIG. 15D, the ear hanger 1500 has a generally cylindrical stem 1510 extending from a first end 1501 to an opposite second end 1502 and a holder 1560 attached to the second end 1502, so that the stem axis 1507 is generally perpendicular to the holder axis 1508. As shown in FIGS. 15A-B, the holder 1560 has a generally cylindrical section 1570 at a first end 1561 that adjoins a generally conical section 1580 at a second end 1562. The cylindrical section 1570 has a relatively wide opening at the first end 1561, which tapers through the conical section 1580 to a relatively narrow opening at the second end 1562. A slit 1564 extends between the ends 1561, 1562 parallel to the holder axis 1508 distal the stem end 1502. The slit 1564 allows the insertion to and removal from the holder 1560 of either the detector cable 905 (FIG. 9) or the emitter cable 906 (FIG. 9) portion of the sensor cable 900 (FIG. 9). The wide opening at the first end 1561 is configured to accommodate a pad bend relief 610 (FIGS. 6A-B). The narrow opening at the second end 1562 is configured to accommodate the detector cable 905 (FIG. 9) or emitter cable 906 (FIG. 9).

As shown in FIG. 15C, the stem 1510 consists of a relatively stiff core 1520 surrounded by a relatively pliable outer layer 1530 so that the stem may be readily bent, yet will retain its shape. Advantageously, the stem 1510 can therefore be formed to accommodate a variety of ear shapes and sizes. The holder 1560 likewise consists of a pliable material 1540. In one embodiment, the core 1520 is a soft temper stainless steel such as #316 and the outer layer 1530 and holder material 1540 are a thermoplastic elastomer, such as AES Santoprene #281-87, which is molded over the core 1520 to form the hanger 1500.

FIGS. 16A-C illustrate a preformed shaping of an ear hanger 1500. FIG. 16A illustrates an unshaped ear hanger 1500, as described with respect to FIGS. 15A-D, above. As shown in FIG. 16B, a generally right angle bend 1610 is made in the stem 1510 proximate the second end 1502 and the holder 1560 and distal the first end 1501. As shown in FIG. 16C, a generally semi-circular bend 1620 is made in the stem 1510 proximate the first end 1501 and distal the second end 1502.

Also shown in FIG. 16C, the preformed ear hanger 1500 has a hook end 1660, a straight middle 1670 and a right angle end 1680. The hook end 1660 is configured to accommodate and comfortably fit the top and back portions of the ear. The right angle end 1680 is configured to position the wide opening at the first end 1561 (FIG. 15A) of the holder 1560 under an earlobe tissue site. The straight middle 1670 is configured to span the length of the ear sensor 300 (FIG. 1) and clip 1200 (FIG. 1) so as to accommodate the ear sensor 300 (FIG. 1) between the holder 1560 and the tissue site 10, as described above.

Although the ear hanger 1500 is described above as configured for the ear sensor 300 (FIG. 1) described herein, one of ordinary skill in the art will recognize that the ear hanger 1500 can be adapted as an attachment supplement for a variety of ear sensor configurations. In particular, the holder 1560 can be shaped, sized, oriented and/or attached along the stem 1510 or otherwise configured to accommodate various ear sensor cables, pads and clips.

FIGS. 17A-E illustrate adhesive tabs used to assist in holding the ear sensor 300 (FIG. 1) to a tissue site 10 (FIG. 1), as described above. As shown in FIG. 17A, a tab carrier 1700 is partitioned into a carrier side 1701 and a cable attachment side 1703. The carrier side 1701 holds multiple tabs 1710. The cable attachment side 1703 defines an opening 1708, which consists of a pattern of apertures and slits configured to accommodate the ear sensor 300 (FIG. 3) through the opening 1708 so that the tab carrier 1700 is slideably retained on the sensor cable 900 (FIG. 9). The carrier side 1701 and cable attachment side 1703 may be separated along a perforation 1706 so that the carrier side 1701 may be quickly and easily removed from the sensor cable 900 (FIG. 9). The remaining cable attachment side 1703 can be removed by sliding it over and off of the sensor cable 900 (FIG. 9). As shown in FIG. 17B, the tab carrier 1700 layers including individual tabs 1710 mounted between a single piece release liner 1720 and multiple piece release covers 1730. As shown in FIGS. 17C-E, an individual tab 1710 includes a double-sided adhesive layer 1712 and a non-adhesive handle 1714. Each tab 1710 is individually removed from the tab carrier 1700 by peeling the tab 1710 from the release liner 1720. Once removed, the tab 1710 can be applied to the ear sensor using the exposed adhesive side. After application, the release cover 1730 is peeled from the tab 1710 to expose the second adhesive side, which adheres to a tissue site 10 (FIG. 1).

FIGS. 18A-F illustrate another ear sensor assembly embodiment comprising an ear boot 1800. The ear boot 1800 is configured to attach an ear sensor 300 (FIG. 3) to a tissue site 10 (FIG. 1) in a manner similar to that described with respect to FIG. 1, above. The ear boot 1800, however, advantageously integrates the features of a clip 1200 (FIGS. 12A-C) and an ear hanger 1500 (FIGS. 15A-D). Specifically, the ear boot 1800 has an ear cover 1801 and a lobe cover 1803. The ear cover 1801 comprises a generally semi-tubular section 1830 defining a corresponding cavity 1840. The ear cover 1801 is configured as semi-circular bend 1810 and an extension 1820 adapted to accommodate the top and back of an ear. The lobe cover 1803 adjoins the ear cover 1801 proximate the extension 1820 and distal the bend 1810.

As shown in FIGS. 18A-F, the lobe cover 1803 has two opposing sensor holders 1860 defining an intervening lobe slot 1870, which is configured to comfortably accommodate an earlobe tissue site 10 (FIG. 1). On faces opposite the lobe slot 1870, each sensor holder 1860 defines a cavity 1880 and a corresponding aperture 1882. Each cavity 1880 is configured to accept and retain a corresponding ear sensor pad 500 (FIGS. 5A-B), either a detector pad 506 (FIGS. 5A-B) or an emitter pad 507 (FIGS. 5A-B). Each aperture 1882 is configured to generally align with each pad window 654 (FIGS. 6A-B) so that light is transmitted between the ear sensor optical components 400 (FIG. 4), 802 (FIG. 8B) through the apertures 1882 and through the tissue site 10:

Also shown in FIGS. 18A-F, each holder 1860 defines a lip 1863 disposed around the end of the cavity 1880 and a pair of catches 1864 located proximate the entrance to the cavity 1880. The ear sensor pads 500 (FIGS. 5A-B) are inserted, one each, into the cavities 1880 so that the holders 1860, and in particular, the lip 1863 and catches 1864 of each holder removably retain the sensor pads 500 (FIGS. 5A-B) on opposite sides of the lobe slot 1870. The ear cover 1801 is then fitted over the ear rim and the lobe slot 1870 is fitted over the earlobe. Alternatively, the ear boot 1800 may be attached to an ear initially and the ear sensor 300 (FIG. 3) installed in the ear boot 1800 afterwards. Although the ear sensor 300 (FIG. 1) is described above and shown in FIG. 1 as attachable to an earlobe, the ear sensor 300 (FIG. 1), ear hanger 1500 (FIGS. 15-16), adhesive tabs 1710 (FIG. 17C) and ear boot 1800 may be adapted for attachment to various other ear tissue sites such as the tragus or portions of the pinna.

FIGS. 19A-D illustrate another embodiment of an ear sensor clip 1900 comprising one or more silicone lenses. The embodiment of an ear sensor clip 1901 shown in FIG. 19 has opposingly positioned housings 1902 and 1903 that house one or more sensor optical components. Each housing 1902 and 1903 comprises an outward facing shell and an inward facing shell. Outward facing shell 1907 and inward facing shell 1906 are two mating halves of the body of housing 1903. Similarly outward facing shell 1904 and inward facing shell 1905 are two mating halves of the body of housing 1902. The two inward facing shells 1905 and 1906 face inward on either side of the patient's earlobe or other suitable tissue site when the oximetry sensor clip is attached to a patient.

In this embodiment the two housings 1903 and 1902 are hingedly connected through hinge supports 1912 and 1914. The holes 1913 and 1915 in the hinge supports 1912 and 1914 are aligned with the spring 1910. Hinge pin 1911 is inserted through the holes 1913 and 1915 and through the spring 1910 so as to rotatably attach the housings 1902 and 1903. The spring 1910 urges the housings to a closed position. The outward facing shells 1904 and 1907 may have ridges 1917 to allow a user to more easily grip the ends of housings 1902 and 1903 when opening the clip by pinching together the open ends of housings 1902 and 1903.

In an embodiment, the inward facing shells 1905 and 1906 further include windows 1919 and 1924 that provide an aperture for transmission of optical energy to or from a tissue site. Translucent silicone material covers windows 1919 and 1924 providing lenses 1920 and 1921. In an embodiment, circular rims 1922 and 1923 on the inward facing shells 1903 and 1902 define regions around windows 1919 and 1924, and lenses 1920 and 1921 formed of a translucent silicone material, substantially cover the regions defined by rims 1922 and 1923.

In an embodiment, the silicone lenses 1920 and 1921 can be formed using injection molding. In the preferred embodiment, the side of each lens that faces the tissue site when clipped onto a patient, has a slightly convex dome shape as shown in lenses 1920A and 1921A; however, the tissue facing side of a lens could alternatively be flat as shown in lenses 1920B and 1921B. Similarly, the side of each lens facing the window 1919 or 1924 can have a number of different shapes such as concave, convex, or flat. The side of each lens facing the window 1919 or 1924 can also have a protrusion that extends into the window 1919 or 1924. The protrusion extending into the window 1919 or 1924 can facilitate assembly of the sensor clip because it can facilitate centering and adhesion when attaching the lens to the inward facing shell 1905 or 1906.

Although a lens in the preferred embodiment has a circular perimeter, in other embodiments, a lens can have a freeform perimeter or a perimeter of another shape such as a square, triangle, or polygon. The molded silicone lenses 1920 and 1921 can be secured to the inward facing shells 1905 and 1906 using silicone adhesive or another substance suitable for bonding silicone to the material used in constructing the inward facing shells 1905 and 1906. Alternatively, the lenses 1920 and 1921 can be configured to fit securely within the rims 1922 or 1923 or to engage the windows 1919 and 1924 so that they can be removably attached to inward facing shells 1905 and 1906 without using adhesive.

In this embodiment, the surfaces of the sensor that have contact with the tissue site are primarily the lenses 1920 and 1921 over windows 1919 and 1924. In an embodiment, the silicone lenses 1920 and 1921 can have a less smooth surface or a textured surface increasing the coefficient of friction between the lenses 1920 and 1921 and the tissue site. This grippy contact surface helps to prevent the sensor clip 1900 from sliding off the patient's earlobe or other suitable tissue site.

In an embodiment, the silicone material can be pliable so that it conforms somewhat to the surface of the tissue site allowing a greater portion of the surface area of the lenses 1920 and 1921 to have contact with the tissue site. In an embodiment, the lenses 1920 and 1921 can also have a larger perimeter to further increase the surface area in contact with the tissue site. The increased area of the contact surface increases the coefficient of friction between the lenses 1920 and 1921 and the tissue site. In addition, better conformity of the lens to the tissue site surface can help eliminate interference and can help to provide a more accurate reading.

Increasing the friction coefficient between contact surfaces of the oximetry sensor and the tissue site can advantageously reduce, for example, the spring tension desired to secure the sensor clip 1900 attached to the patient's earlobe or other suitable tissue site. As will be recognized from the disclosure herein, applying less pressure to the tissue site can advantageously reduce pressure necrosis, and can advantageously increase patient comfort.

In an embodiment, a thin sheet of opaque material can be placed inside either housing 1902 or 1903 between the optical components and the inward facing shell 1905 or 1906. The thin sheet of opaque material is located beneath window 1919 or 1924, and a window in the opaque material provides an aperture for transmission of optical energy to or from the tissue site. The opaque material blocks light, and the window in the opaque material can be sized as needed to block the proper amount of light from entering the aperture to, for example, avoid saturation of the light detector. In one embodiment, the opaque material is a thin sheet of metal.

Opening 1918 in shells 1906 and 1907 of housing 1903 provides space for the ear sensor cable 900 that electrically connects the optical components inside of housing 1903 with a sensor connector 1000. Cable 1925 allows communication between the optical components in housings 1902 and 1903.

A pulse oximetry ear sensor has been disclosed in detail in connection with various embodiments. These embodiments are disclosed by way of examples only and are not to limit the scope of the claims that follow. One of ordinary skill in the art will appreciate many variations and modifications.

Additionally, all publications, patents, and patent applications mentioned in this specification are herein incorporated by reference to the same extent as if each individual publication, patent, or patent application was specifically and individually indicated to be incorporated by reference.

What is claimed is:

1. An ear sensor for providing one or more intensity signals representative of at least one physiological parameter of pulsing blood, the ear sensor comprising:
   an emitter which emits light of at least first and second wavelengths;
   a light-sensitive detector which provides intensity signals resulting from detection of the at least first and second wavelengths of the light after the light is attenuated by body tissue carrying pulsing blood;
   a clip housing including one or more windows through which the light or the attenuated light will pass, wherein the clip housing also houses the emitter and the detector in movable proximity to one another; and
   a plurality of tissue contacting surfaces configured to be positioned between the emitter and the tissue and between the detector and the tissue when the clip housing is applied to a measurement site, wherein the tissue contacting surfaces comprise silicone lenses and wherein said silicone lenses comprise a substantially translucent textured surface that increases a coefficient of friction between the silicone lenses and a tissue site.

2. The ear sensor according to claim 1, wherein said silicone lenses are pliable thereby increasing a surface area contacting the skin.

3. The ear sensor according to claim 1, wherein at least one of said silicone lenses is sized to have a surface area greater than a surface area defined by at least one of the windows.

4. The ear sensor according to claim 1, wherein optical properties of said silicone lenses are substantially similar to optical properties of glass.

5. The ear sensor according to claim 1, wherein said silicone lenses are injection molded.

6. The ear sensor according to claim 1, wherein said silicone lenses are one of partially hemispherical and convex in shape.

7. The ear sensor according to claim 1, wherein said silicone lenses are disk shaped.

8. The ear sensor according to claim 1, wherein said silicone lenses are rectangular.

9. The ear sensor according to claim 1, wherein said clip housing comprises a disposable clip and said emitter and detector are removable from said disposable clip.

10. The ear sensor according to claim 1 further comprising an attachment supplement, wherein the attachment supplement comprises an ear hanger adapted to fit around an ear portion so as to support at least a portion of the ear sensor weight.

11. The ear sensor according to claim 1 further comprising an attachment supplement, wherein the attachment supplement comprises an ear hanger comprising:
   a formable stem having a first end and having a second end;
   a generally semi-circular bend proximate said first end;

a generally right angle bend proximate said second end; and a holder attached to second end and configured to accommodate a cable.

12. The ear sensor according to claim 1, wherein, in a closed position, said clip housing exerts a force on said tissue in the range of about 90 gram force to about 140 gram force.

13. The ear sensor according to claim 1, wherein, in a closed position, said clip housing exerts a force on a tissue site in the range of about 115 gram force to about 130 gram force.

14. An oximetry sensor comprising:
a plurality of opposing members each housing one of an emitter and a detector, and each including one or more windows covered by one or more silicone lenses, wherein said plurality of opposing members are configured to removably position said silicone lenses against the suitable tissue site and wherein said silicone lenses comprise a substantially translucent textured surface configured to aid in reducing movement of the sensor when the sensor is positioned against the tissue site.

15. The oximetry sensor of claim 14, wherein the plurality of opposing members is capable of removably positioning said silicone lenses against a patient's ear.

16. The oximetry sensor of claim 15, wherein opposing members further comprise a plurality of extended ridges adapted to assist in releasing said plurality of opposing members from said tissue site.

17. The ear sensor according to claim 14 further comprising an attachment supplement.

* * * * *

UNITED STATES PATENT AND TRADEMARK OFFICE
CERTIFICATE OF CORRECTION

PATENT NO. : 7,341,559 B2
APPLICATION NO. : 10/631882
DATED : March 11, 2008
INVENTOR(S) : Christian Schulz, Massi E. Kiani and Eugene Mason It is certified that error appears in the above-identified patent and that said Letters Patent is hereby corrected as shown below:

At Column 2, Line 61 Delete "innerjaw;" and insert -- inner jaw; --, therefor.

At Column 3, Line 3 After "tab;" delete "and"

At Column 3, Line 4 After "handle;" delete "and".

At Column 3, Line 7 Delete "boot." and insert -- boot; and --, therefor.

At Column 5, Line 34 Before "emitter" delete "a" and insert -- an --, therefor.

At Column 6, Line 24 Delete "1B," and insert -- 11B, --, therefor.

At Column 8, Line 12 Delete "Gycology#6200." and insert -- Cycology#6200. --, therefor.

At Column 10, Line 6 After "site" delete "10:" and insert -- 10. --, therefor.

Signed and Sealed this

Twenty-third Day of September, 2008

JON W. DUDAS
*Director of the United States Patent and Trademark Office*